United States Patent
Lin et al.

(10) Patent No.: US 10,851,068 B2
(45) Date of Patent: Dec. 1, 2020

(54) METHOD FOR PREPARING PYRIMIDONE COMPOUND

(71) Applicant: SUNSHINE LAKE PHARMA CO., LTD., Dongguan (CN)

(72) Inventors: Runfeng Lin, Dongguan (CN); Xiaojun Wang, Dongguan (CN); Jihua Lin, Dongguan (CN); Liang Chen, Dongguan (CN); Yingjun Zhang, Dongguan (CN); Jiancun Zhang, San Mateo, CA (US)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 16/627,966

(22) PCT Filed: Jul. 3, 2018

(86) PCT No.: PCT/CN2018/094325
§ 371 (c)(1),
(2) Date: Dec. 31, 2019

(87) PCT Pub. No.: WO2019/011163
PCT Pub. Date: Jan. 17, 2019

(65) Prior Publication Data
US 2020/0157054 A1  May 21, 2020

(30) Foreign Application Priority Data
Jul. 14, 2017 (CN) .......................... 2017 1 0572527

(51) Int. Cl.
C07D 239/36  (2006.01)
C07D 211/50  (2006.01)
C07C 211/50  (2006.01)

(52) U.S. Cl.
CPC .......... *C07D 239/36* (2013.01); *C07C 211/50* (2013.01)

(58) Field of Classification Search
CPC ........................... C07D 239/36; C07C 211/50
USPC ........................................................ 544/298
See application file for complete search history.

(56) References Cited

U.S. PATENT DOCUMENTS

| 9,434,695 B2 | 9/2016 | Zhang et al. |
| 9,902,712 B2 | 2/2018 | Zhang et al. |
| 2007/0203203 A1 | 8/2007 | Tao et al. |
| 2019/0308939 A1 | 10/2019 | Lin et al. |
| 2020/0157054 A1* | 5/2020 | Lin ....................... C07C 209/10 |

FOREIGN PATENT DOCUMENTS

WO  2018/019244 A1  2/2018

OTHER PUBLICATIONS

Sep. 29, 2018 Search Report issued in International Patent Application No. PCT/CN2018/094325.
Sep. 29, 2018 Written Opinion of the International Seaching Authority issued in International Patent Application No. PCT/CN2018/094325.

* cited by examiner

*Primary Examiner* — Venkataraman Balasubramanian
(74) *Attorney, Agent, or Firm* — Oliff PLC

(57) ABSTRACT

A method for preparing a pyrimidone compound and an important intermediate in which raw materials of the preparation method are cheap, the reaction condition of preparation method is mild, the preparation method is simple to operate, and is safe and controllable, has high total yield, and thus is suitable for industrial production.

22 Claims, No Drawings

METHOD FOR PREPARING PYRIMIDONE COMPOUND

CROSS-REFERENCE TO RELATED APPLICATION

This application claims priority and benefit of Chinese Patent Application No. 201710572527.5, filed with State Intellectual Property Office on Jul. 14, 2017, which is hereby incorporated by reference in its entirety.

FIELD

The invention relates to the field of medicinal chemistry, in particular to the methods for preparing a pyrimidone compound named 3-(4-(dihexylamino)-3-fluorophenyl)-2,6-dimethylpyrimidin-4(3H)-one and hydrochloride thereof.

BACKGROUND

Fibrosis is the formation of excess fibrous connective tissue in an organ or tissue in a reparative or reactive process. The fibrosis of the organ tissue in less serious cases is called fibrosis, and in severe cases can result in tissue damage and cause organ sclerosis. Tissue fibrosis occurs not only in organs such as the lung, liver, heart, kidney, but also in almost all organs and systems of the human body. About one third of the world's people die of tissue fibrosis and organ failure caused by tissue fibrosis.

Patent applications WO 2014012360 and CN 103570630 disclosed azacyclic derivatives having antifibrotic action, in which the compound named 3-(4-(dihexylamino)-3-fluorophenyl)-2,6-dimethylpyrimidin-4(3H)-one (represented by Formula (II)) can effectively prevent or treat tissue fibrosis in humans or animals.

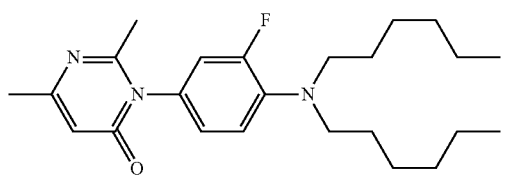

(II)

The above patent applications also disclosed a method for preparing the compound having formula (II) comprising reacting 3,4-difluoronitrobenzene with dihexylamine in the presence of potassium carbonate in DMSO to give a 4-substituted nitrobenzene compound, which is then undergone hydrogenation reduction catalyzed by Pd/C to obtain a 4-substituted aniline compound, and finally reacting the 4-substituted aniline compound with methyl 3-acetylaminocrotonate in the presence of trimethyl aluminum to give the compound having formula (II); the reaction process is as follows.

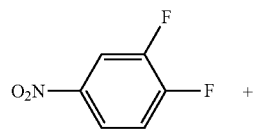

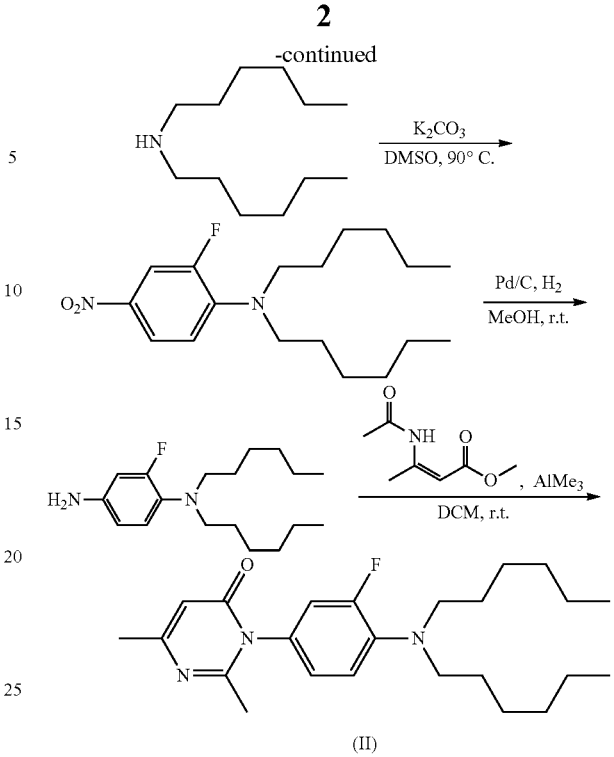

A high-priced metal palladium catalyst and flammable and explosive trimethylaluminum are used in the method above. Therefore, the synthetic method is expensive and dangerous to operate and unsuitable for scale-up production. In addition, the compound having Formula (II) is easily deteriorated under normal temperature and pressure conditions and thus hardly preserved. In addition, the overall yield of the method above is low and only 34%.

Therefore, further researches of the preparation method of the compound having Formula (II) favorable for the industrial production, of which the cost is low, the operation is simple and the conditions are mild, are needed.

SUMMARY OF THE INVENTION

The present invention relates to a method for preparing a compound having Formula (II) or hydrochloride thereof (i.e., a compound having Formula (I)), and also relates to important intermediates therein and a method for their preparation. The method of the present invention has mild conditions, is simple to operate, is safe and controllable, and has a high yield, and is suitable for industrial production. The obtained hydrochloride of the compound having Formula (II) (i.e., Formula (I)) is stable at room temperature under normal pressure, and thus easy to preserve and suitable for preparing medicine.

Specifically, provided herein is a method for preparing a compound having Formula (II) or Formula (I) (i.e., 3-(4-(dihexylamino)-3-fluorophenyl)-2,6-dimethylpyrimidin-4(3H)-one or hydrochloride thereof) comprising reacting 3,4-difluoronitrobenzene with dihexylamine in the presence of a base to give a 4-substituted nitrobenzene compound, and reducing the 4-substituted nitrobenzene compound in the presence of a reductant to give a 4-substituted aniline compound, and then reacting the 4-substituted aniline compound with a suitable reagent to give a hydrochoride compound having Formula (V); reacting the compound having Formula (V) with diketene or an acetoacetate to give a N-substituted aniline compound; then reacting the N-substituted aniline compound with a solution of ammonia in alcohol or an ammonium salt to give a product, and then reacting the product with triethyl orthoacetate to give the compound having Formula (II). In addition, in order to easy to preserve, the compound having Formula (I) can be obtained by acidifying the compound having Formula (II).

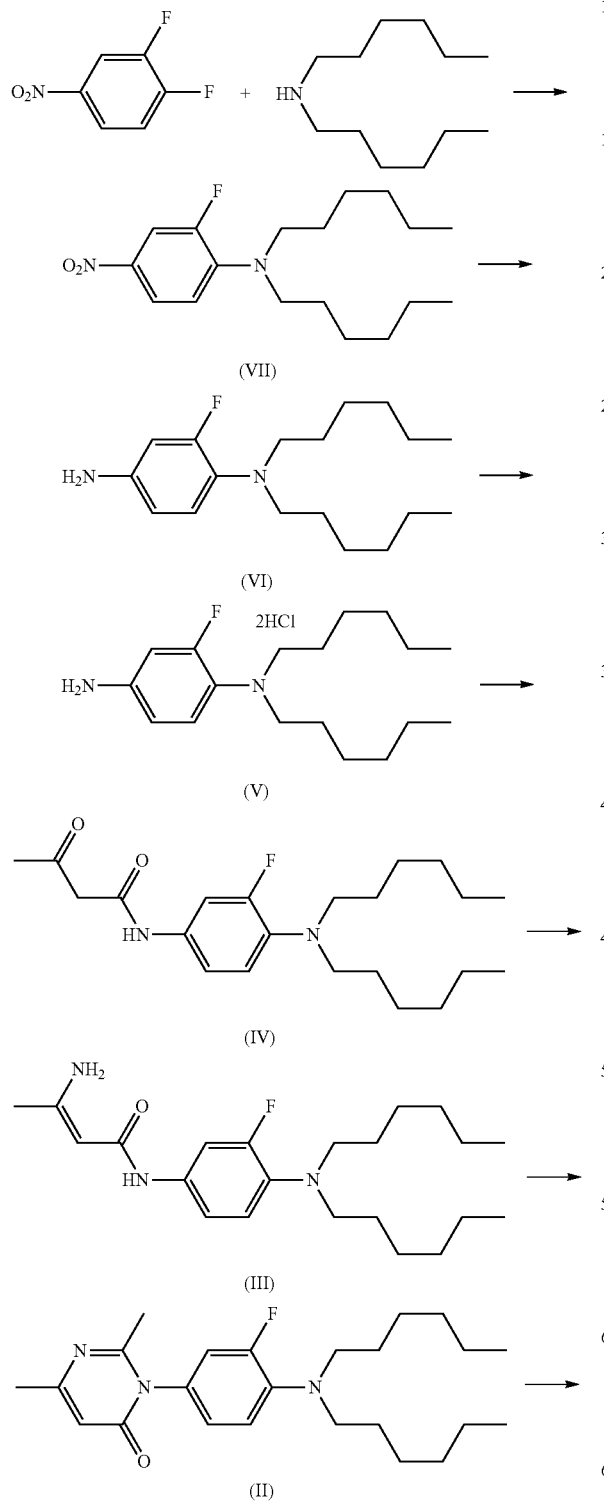

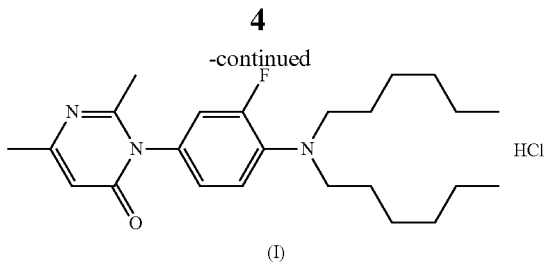

In the method of the present invention, a metal catalyst such as Zn or Fe, or a sulfide reagent, which is lower in price than the metal palladium catalyst, is used in the nitro reduction leading to the decrease of the production cost. Meanwhile, the aniline compound obtained by the nitro reduction is directly acidized to give the corresponding hydrochloride, of which the preparation process is simple, and as a result complicated post-treatment processes are avoided. And the hydrochloride obtained has stable properties, high purity, and is easy to preserve and favorable to the control of the next reaction (the impurities generated in the subsequent reaction can be further controlled) and the improvement of the yield of the next reaction. The cyclization reaction after nitro reduction in the prior art is improved in the method of the present invention: the use of flammable and explosive trimethylaluminum reagent is avoided to make the reaction more safe and controllable. Finally, the pyrimidine ketone compound having Formula (II) in the present invention is acidified to obtain the corresponding hydrochloride, which is stable and easy to preserve. In summary, the method of the invention has the advantages of cheap raw materials, low cost, mild conditions, simple operation, high total yield, and is safe. The overall yield of the seven steps for preparing the compound of Formula (I) starting from 3,4-difluoronitrobenzene under the conditions of small quantities can be high to 80%, and it can still reach 50%-60% in the large scale productions. Therefore, the method above is controllable and thus particularly suitable for industrial production.

The invention also relates to two important intermediates (compound having Formula (II-a) and compound having Formula (V)) in the method for preparing the compound having Formula (I) and the preparation methods thereof,

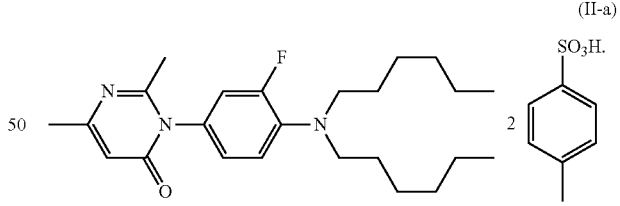

In one aspect, provided herein is a compound having Formula (I),

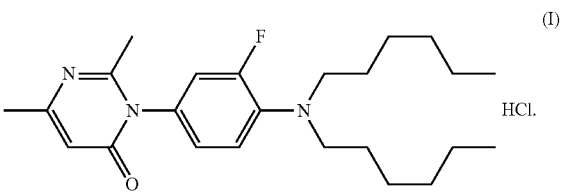

In another aspect, further provided herein is a method for preparing the compound having Formula (II) comprising reacting a compound having Formula (III) with triethyl orthoacetate to give the compound having Formula (II),

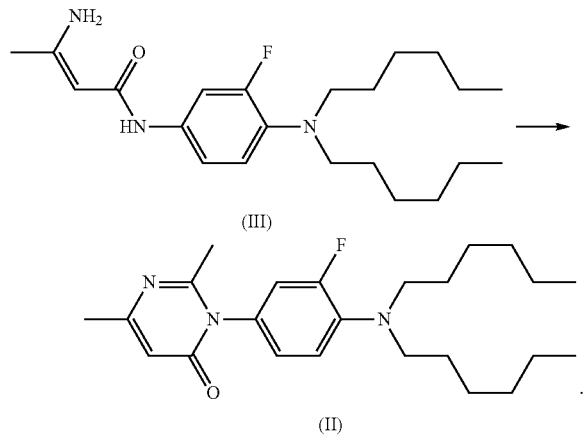

In some embodiments, the compound having Formula (III) can react with triethyl orthoacetate in solvent 4 to give the compound having Formula (II). In some embodiments, the solvent 4 disclosed herein includes but is not limited to, toluene, xylene, or any combination thereof.

In some embodiments, the method for preparing the compound having Formula (II) comprises that the compound having Formula (III) reacts with triethyl orthoacetate without solvent. The term "without solvent" refers to the reaction is carried out in the absence of a solvent or using a certain reagent of the reaction as a solvent (without other solvent); specifically, the certain reagent of the reaction can be triethyl orthoacetate used in the invention.

In some embodiments, the reaction disclosed herein for preparing the compound having Formula (II) is carried out by heating. In some embodiments, the heating disclosed herein is heating to 80° C.-140° C., or 80° C.-120° C., or 100° C.-120° C., or heating to about 80° C., 100° C., 115° C., 120° C., 125° C., 130° C. or 140° C.

In some embodiments, the reaction disclosed herein for preparing the compound having Formula (II) is carried out at 80° C.-140° C. In some embodiments, the reaction disclosed herein for preparing the compound having Formula (II) is carried out at 100° C.-130° C. In some embodiments, the reaction disclosed herein for preparing the compound having Formula (II) is carried out at 80° C.-120° C. In some embodiments, the reaction disclosed herein for preparing the compound having Formula (II) is carried out at 100° C.-120° C. In some embodiments, the reaction disclosed herein for preparing the compound having Formula (II) is carried out at 80° C.-100° C. In some embodiments, the reaction disclosed herein for preparing the compound having Formula (II) is carried out at about 80° C., 100° C., 115° C., 120° C., 125° C., 130° C. or 140° C.

The amount of triethyl orthoacetate used in the method of the invention is multiple molar equivalents relative to the amount of the compound having Formula (III), including but not limited to about 2.0 molar equivalents, 3.0 molar equivalents, 4.0 molar equivalents, and 5.0 molar equivalents, or more than 5.0 molar equivalents. In some embodiments, the amount of triethyl orthoacetate disclosed herein is 2.0 to 4.0 molar equivalents relative to the amount of the compound having Formula (III), wherein the term "2.0 to 4.0 molar equivalents" includes but is not limited to 2.0 molar equivalents, 3.0 molar equivalents or 4.0 molar equivalents. In some embodiments, the amount of triethyl orthoacetate disclosed herein is about 2.0 molar equivalents, 2.5 molar equivalents, 3.0 molar equivalents, 3.5 molar equivalents or 4.0 molar equivalents relative to the amount of the compound having Formula (III).

In some embodiments, the time of the reaction disclosed herein for preparing the compound having Formula (II) is 1 to 24 hours. In some embodiments, the time of the reaction disclosed herein for preparing the compound having Formula (II) is longer than 24 hours. In some embodiments, the time of the reaction disclosed herein for preparing the compound having Formula (II) is 4 to 24 hours. In some embodiments, the time of the reaction disclosed herein for preparing the compound having Formula (II) is about 1, 2, 4, 6, 8 or 24 hours.

As described in the invention, the reaction for preparing the compound having Formula (II) by reacting compound having Formula (III) with triethyl orthoacetate is carried out by heating, and the different reaction temperature has different effect on the reaction; when the reaction is carried out at about 100° C. to about 120° C., especially at about 120° C., the yield is high.

The compound having Formula (II) prepared by the method of the invention described above can be directly used for preparing the compound having Formula (I), or can be further purified and then used for preparing the compound having Formula (I). The preparation method of the present invention further comprises purifying the compound having Formula (II) by acidifying and alkalizing in sequence; the purification is simple and controllable, and is favorable for the control of the next reaction. The purified product (purified compound having Formula (II)) obtained after the purification described above can further react with hydrogen chloride or a solution thereof to obtain the hydrochloride of Formula (I) in high yield and high purity.

In some embodiments, the method for preparing the compound having Formula (II) disclosed herein, wherein the compound having Formula (II) can be further purified by the following steps:

Step (A-I): Acidification—Reacting the compound having Formula (II) prepared by the method of the invention with a suitable acid or a hydrate thereof in a suitable solvent to give a compound having Formula (II-b);

Step (B-I): Alkalization—Reacting the compound having Formula (II-b) in the presence of a base in a suitable solvent to give the purified compound having Formula (II);

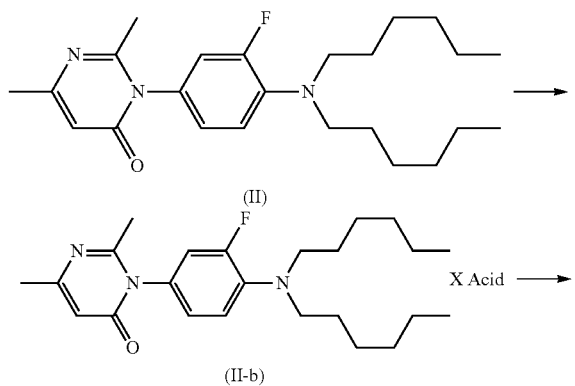

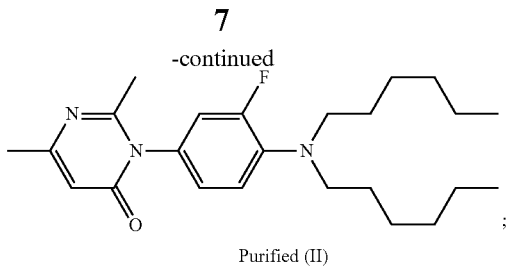

Purified (II)

wherein the suitable acid is an acid which can form a stable salt with the compound having Formula (II), and can be an organic acid or inorganic acid, including but not limited to, sulfuric acid, oxalic acid, acetic acid, benzenesulfonic acid, p-toluenesulfonic acid, benzoic acid, p-methylbenzoic acid, maleic acid, fumaric acid, tartaric acid, malic acid, and the like. X represents the number of molecules of the acid in the salt formed by the acid and the compound having Formula (II). For example, if the suitable acid is p-toluenesulfonic acid, then X may be 2.

In other embodiments, the method for preparing the compound having Formula (II) disclosed herein, wherein the compound having Formula (II) can be further purified by the following steps:

Step (A): Reacting the compound having Formula (II) prepared by the method of the invention with p-toluenesulfonic acid or a p-toluenesulfonic acid hydrate to give a compound having Formula (II-a);

Step (B): Reacting the compound having Formula (II-a) in the presence of base 1 to give the purified compound having Formula (II);

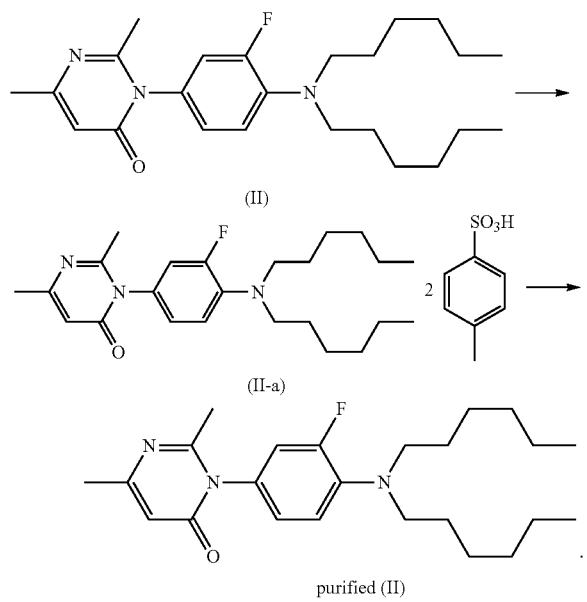

In some embodiments, the solvent 1 disclosed herein is an alcohol, an ether, a ketone, an ester, a halogenated hydrocarbon, toluene, acetonitrile, water, or any combination thereof. In other embodiments, the solvent 1 disclosed herein is dichloromethane, acetonitrile, toluene, methanol, ethanol, isopropanol, 1-propanol, n-butanol, tetrahydrofuran, t-butanol, ethyl acetate, isobutanol, isopentanol, n-propyl acetate, isopropyl acetate, 4-methyl-2-pentanone, dimethyl phthalate, methyl methacrylate, 1,4-dioxane, ethyl formate, xylene, water, or any combination thereof.

In some embodiments, the p-toluenesulfonic acid hydrate is p-toluenesulfonic acid monohydrate.

In some embodiments, the reaction in step (A) disclosed herein is carried out at room temperature or by heating. In some embodiments, the heating disclosed herein is heating to about 82° C., i.e., the reaction in step (A) disclosed herein is carried out at about 82° C. In some embodiments, the reaction in step (A) disclosed herein is carried out at 25° C.-82° C. In some embodiments, the reaction in step (A) disclosed herein is carried out at room temperature or about 82° C. In some embodiments, the reaction in step (A) disclosed herein is carried out at about 25° C., 50° C. or 82° C.

In some embodiments, the solvent 2 disclosed herein is an alcohol, acetonitrile, water, or any combination thereof. In some embodiments, the solvent 2 disclosed herein is methanol, ethanol, isopropanol, tert-butanol, acetonitrile, water, or any combination thereof.

In some embodiments, the base 1 disclosed herein may be an organic base or inorganic base. In other embodiments, the base 1 disclosed herein is an inorganic base including, but not limited to, potassium carbonate, sodium carbonate, sodium hydroxide, potassium hydroxide, lithium hydroxide, sodium bicarbonate, potassium bicarbonate or any combination thereof. The base 1 disclosed herein can be directly used in the reaction in the form of a solid, or in the form of a solution with a certain concentration which is formulated previously, wherein the solution with a certain concentration includes, but is not limited to saturated aqueous solution, etc.

In some embodiments, the reaction in step (B) disclosed herein is carried out at room temperature or by heating. In some embodiments, the heating disclosed herein is heating to about 77° C. or 82° C. In some embodiments, the reaction in step (B) disclosed herein is carried out at room temperature, or by heating to about 77° C. or 82° C. In some embodiments, the reaction in step (B) disclosed herein is carried out at 25° C.-85° C. In some embodiments, the reaction in step (B) disclosed herein is carried out at 25° C.-82° C. In some embodiments, the reaction in step (B) disclosed herein is carried out at 30° C.-82° C. In some embodiments, the reaction in step (B) disclosed herein is carried out at about 25° C., 30° C., 77° C. or 82° C.

In some embodiments, the method for preparing the compound having Formula (II) disclosed herein further comprises a method for preparing the compound having Formula (III) which comprises reacting a compound having Formula (IV) with a solution of ammonia in alcohol or an ammonium salt in solvent 5 to give the compound having Formula (III),

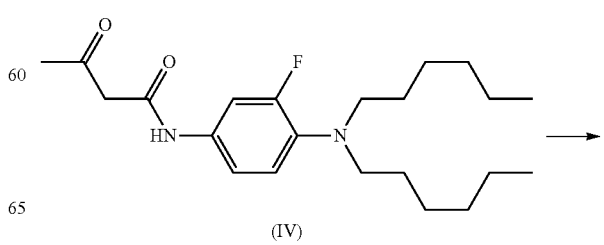

-continued

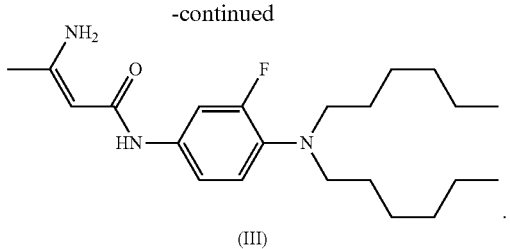

(III)

In some embodiments, the solvent 5 disclosed herein is an alcohol, water, or any combination thereof. In some embodiments, the solvent 5 disclosed herein is methanol, ethanol, isopropanol, water, or any combination thereof.

In some embodiments, the solution of ammonia in alcohol disclosed herein is a solution of ammonia in methanol, a solution of ammonia in ethanol or a solution of ammonia in isopropanol. The amount of ammonia in the solution of ammonia in alcohol is a multiple molar equivalents relative to the amount of the compound having Formula (IV). In some embodiments, the amount of the ammonia in the solution of ammonia in methanol disclosed herein is 2.0 to 4.0 molar equivalents relative to the amount of the compound having Formula (IV). In some embodiments, the amount of the ammonia in the solution of ammonia in methanol disclosed herein is about 2.0, 3.0 or 4.0 molar equivalents relative to the amount of the compound having Formula (IV). The amount of the solution of ammonia in methanol can be calculated based on the molar amount of ammonia and the concentration of the solution.

In some embodiments, the ammonium salt described herein includes, but is not limited to, ammonium chloride, ammonium bromide, ammonium acetate, ammonium formate or ammonium bicarbonate, and the like.

In some embodiments, the compound having Formula (IV) disclosed herein can directly react with an ammonium salt to give the target compound having Formula (III). In some embodiments, the reaction of the compound having Formula (IV) with an ammonium salt is carried out in the presence of base a; wherein the base a includes, but is not limited to triethylamine, N,N-diisopropylethylamine, pyridine, potassium carbonate, sodium carbonate, sodium hydroxide, potassium hydroxide, lithium hydroxide, sodium bicarbonate, potassium bicarbonate, or any combination thereof. The base a disclosed herein can be directly used in the reaction in the form of a solid or liquid, or in the form of a solution with a certain concentration which is formulated previously, wherein the solution with a certain concentration includes, but is not limited to saturated aqueous solution, etc.

In some embodiments, the reaction disclosed herein for preparing the compound having Formula (III) is carried out at room temperature or by heating. In some embodiments, the heating disclosed herein is heating to about 40° C. or 65° C. In some embodiments, the reaction disclosed herein for preparing the compound having Formula (III) is carried out at 20° C.-65° C. In some embodiments, the reaction disclosed herein for preparing the compound having Formula (III) is carried out at 20° C.-40° C. In some embodiments, the reaction disclosed herein for preparing the compound having Formula (III) is carried out at room temperature or 40° C.-65° C. In some embodiments, the reaction disclosed herein for preparing the compound having Formula (III) is carried out at room temperature or about 20° C., 25° C., 40° C. or 65° C.

In some embodiments, the method for preparing the compound having Formula (III) comprises reacting the compound having Formula (IV) with a solution of ammonium in alcohol in solvent 5 to give the compound having Formula (III); wherein, the solvent 5 includes but is not limited to methanol; the solution of ammonium in alcohol includes but is not limited to a solution of ammonium in methanol; the reaction of the compound having Formula (IV) with a solution of ammonium in alcohol is carried out at room temperature or at 20° C.-65° C. (including but not limited to 20° C., 40° C. or 65° C.) or at 40° C.-65° C.; the amount of the ammonia in the solution of ammonia in methanol is as defined herein.

In some embodiments, the method for preparing the compound having Formula (III) comprises reacting the compound having Formula (IV) with an ammonium salt in solvent 5 to give the compound having Formula (III). Wherein, the solvent 5 includes but is not limited to, methanol, ethanol, isopropanol, water or any combination thereof; the ammonium salt includes but is not limited to ammonium acetate and ammonium bicarbonate; the reaction of the compound having Formula (IV) with the ammonium salt is carried out at 25° C.-65° C. or 25° C.-40° C., or about 25° C. or 40° C. Furthermore, the reaction of the compound having Formula (IV) with the ammonium salt can be carried out in the presence of a base (such as potassium carbonate, etc.): for example, the compound having Formula (IV) can react with ammonium acetate in the presence of sodium carbonate to give the compound having Formula (III); or, the reaction of the compound having Formula (IV) with the ammonium salt can also be carried out in the absence of a base: for example, the compound having Formula (IV) can directly react with ammonium bicarbonate to give the compound having Formula (III). The ammonium salt used in the reaction of the compound having Formula (IV) with an ammonium salt in the invention is cheap and easy to obtain, and it is easy to reserve and transport, and suitable for industrial production.

In some embodiments, the method for preparing the compound having Formula (III) disclosed herein further comprises a method for preparing the compound having Formula (IV) which comprises reacting a compound having Formula (V) with diketene or an acetoacetate in solvent 6 to give the compound having Formula (IV),

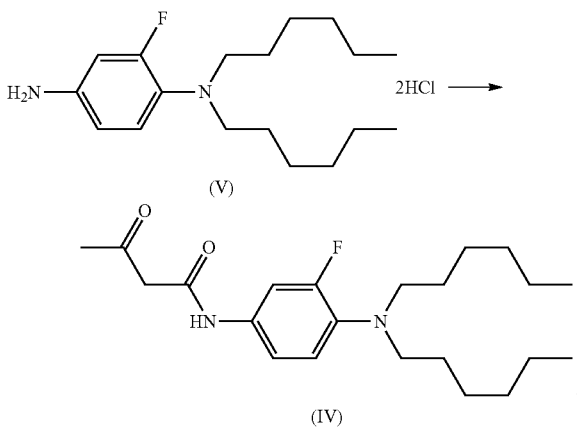

In some embodiments, the solvent 6 disclosed herein includes but is not limited to, dichloromethane, tetrahydrofuran, toluene, acetone, acetonitrile, water, or any combination thereof.

In some embodiments, the reaction disclosed herein for preparing the compound having Formula (IV) is carried out in the presence of base 2, wherein the base 2 is an organic base or an inorganic base. In some embodiments, the reaction for preparing the compound having Formula (IV) is carried out in the presence of base 2; wherein the base 2 includes, but is not limited to triethylamine, pyridine, N,N-diisopropylethylamine, methylmorpholine, potassium carbonate, sodium carbonate, sodium hydroxide, potassium hydroxide, lithium hydroxide, sodium bicarbonate, potassium bicarbonate, or any combination thereof. The base 2 disclosed herein can be directly used in the reaction in the form of a solid or liquid, or in the form of a solution with a certain concentration which is formulated previously, wherein the solution with a certain concentration includes, but is not limited to saturated aqueous solution, etc.

In some embodiments, the reaction for preparing the compound having Formula (IV) disclosed herein, wherein the compound having Formula (V) mixes with diketene (or an acetoacetate) and base 2 directly, and then the mixture reacts under a suitable condition to give the target product. In some embodiments, the reaction for preparing the compound having Formula (IV) disclosed herein, wherein the compound having Formula (V) firstly reacts with the first base 2 (such as potassium carbonate, sodium carbonate, etc.) to give a free amine, then the free amine reacts with an acetoacetate in the presence of the second base 2 (such as triethylamine, pyridine, DIPEA, methylmorpholine, etc.) to give the compound having Formula (IV).

In some embodiments, the reaction disclosed herein for preparing the compound having Formula (IV) is carried out at a low temperature, at room temperature, or by heating. In some embodiments, the reaction disclosed herein for preparing the compound having Formula (IV) is carried out at 0° C.-120° C. In some embodiments, the reaction disclosed herein for preparing the compound having Formula (IV) is carried out at 0° C.-110° C. In some embodiments, the reaction disclosed herein for preparing the compound having Formula (IV) is carried out at 25° C.-110° C. In some embodiments, the reaction disclosed herein is carried out at 25° C.-80° C. In some embodiments, the reaction disclosed herein is carried out at about 0° C., 5° C., 25° C., 42° C., 60° C., 80° C., 105° C. or 110° C.

In some embodiments, the method for preparing the compound having Formula (IV), wherein the compound having Formula (V) can react with diketene at a low temperature to give the compound having Formula (IV) in high yield. For example, the compound having Formula (V) can react with diketene at about 0° C. (such as under an ice-bath condition) or room temperature to give the compound having Formula (IV) in high yield; or, the compound having Formula (V) can react with diketene by heating to a low temperature such as about 42° C., and give a high yield.

In some embodiments, the method for preparing the compound having Formula (IV), wherein the compound having Formula (V) can react with an acetoacetate (including but not limited to, methyl acetoacetate or tert-butyl acetoacetate) by heating, and the heating refers to heating to about 105° C. to about 110° C., preferably about 105° C. or about 110° C. The reaction of the compound having Formula (V) with an acetoacetate is simple in operation, simple in post-treatment, and has a high yield; wherein the acetoacetate (including but not limited to, methyl acetoacetate or tert-butyl acetoacetate) used is stable in nature, low irritating, safe and reliable, and thus suitable for industrial production.

In some embodiments, the amount of the diketene disclosed herein is 1.0 to 2.0 molar equivalents relative to the amount of the compound having Formula (V). In some embodiments, the amount of the diketene disclosed herein is about 1.0 molar equivalents, 1.2 molar equivalents, 1.5 molar equivalents or 2.0 molar equivalents relative to the amount of the compound having Formula (V).

In some embodiments, the base 2 disclosed herein is added dropwise into the mixture of the compound having Formula (V) and diketene. In some embodiments, the base 2 disclosed herein firstly is mixed with the compound having Formula (V) in solvent 6, then diketene is added dropwise into the mixture at a certain temperature, and the temperature of the reaction system needs to be controlled (generally the temperature of the reaction system is controlled not to exceed the boiling point of the solvent used) because it increases during the adding process. In some embodiments, the temperature of the reaction system needs to be controlled to ≤30° C. In some embodiments, the temperature of the reaction system needs to be controlled to ≤5° C.

In some embodiments, the acetoacetate disclosed herein includes but is not limited to methyl acetoacetate, ethyl acetoacetate, isopropyl acetoacetate or tert-butyl acetoacetate.

In some embodiments, the method for preparing the compound having Formula (IV) disclosed herein further comprises a method for preparing the compound having Formula (V) which comprises reacting a compound having Formula (VI) with a suitable reagent in solvent 7 to give the compound having Formula (V),

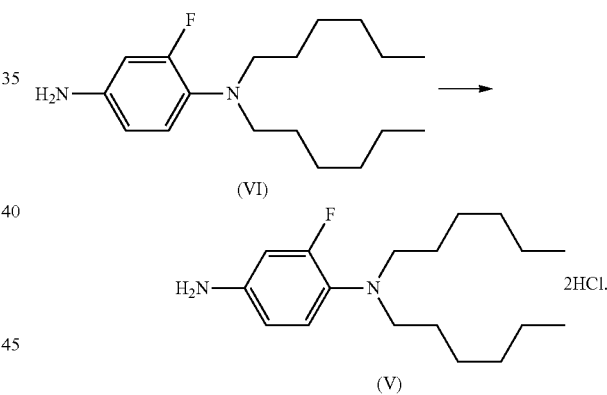

In some embodiments, the solvent 7 disclosed herein is ethyl acetate, acetone, toluene, acetonitrile, methanol, ethanol, dichloromethane, or any combination thereof.

In some embodiments, the suitable reagent disclosed herein is hydrogen chloride or a hydrogen chloride solution, $Me_3SiCl$ or $SOCl_2$.

In some embodiments, the reaction disclosed herein for preparing the compound having Formula (V) is carried out at room temperature. In some embodiments, the reaction disclosed herein is carried out at about 25° C.

In some embodiments, the hydrogen chloride solution disclosed herein is a solution of hydrogen chloride in water, a solution of hydrogen chloride in ethyl acetate or a solution of hydrogen chloride in isopropanol, or any combination thereof.

The method for preparing the compound having Formula (V) of the present invention is simple, safe and reliable, and has a high product yield. For example, the total yield of the three-step reaction for preparing the compound having Formula (V) starting from 3,4-difluoronitrobenzene and dihexylamine under the condition of large amounts can still reach more than 90%.

The method for preparing the compound having Formula (V) from the compound having Formula (VI) of the invention can obtain a high-purity hydrochloride product, which is favorable for the control of the next reaction, and reduces the by-product generated in the subsequent reaction step, thereby improves the yield of the whole preparation process. In general, the method can effectively reduce the cost for preparing the compound having Formula (II) and improve the yield at the same time.

In some embodiments, the method for preparing the compound having Formula (V) disclosed herein further comprises a method for preparing the compound having Formula (VI),

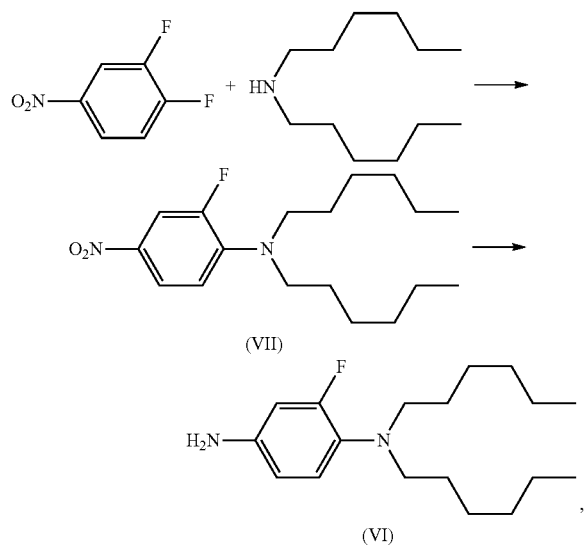

which comprises the following steps:

Step (i): Reacting 3,4-difluoronitrobenzene with dihexylamine in the presence of base 3 in solvent 8 to give a compound having Formula (VII), wherein the solvent 8 is not DMSO which is hardly worked up; and Step (ii): Reacting the compound having Formula (VII) in the presence of a reductant in solvent 9 to give the compound having Formula (VI), wherein the reductant is not costly Pd/C.

In some embodiments, the solvent 8 is N,N-dimethylformamide, dichloromethane, toluene, ethyl acetate, acetonitrile, acetone, isopropanol, ethanol, or any combination thereof.

In some embodiments, the base 3 disclosed herein is an inorganic base or organic base, including but not limited to, lithium hydroxide or a hydrate thereof, sodium carbonate, potassium carbonate, sodium bicarbonate, potassium bicarbonate, potassium phosphate, sodium phosphate, sodium hydroxide, potassium hydroxide, triethylamine, pyridine, or any combination thereof. The base 3 disclosed herein can be directly used in the reaction in the form of a solid or liquid, or in the form of a solution with a certain concentration which is formulated previously, wherein the solution with a certain concentration includes, but is not limited to saturated aqueous solution, etc.

In some embodiments, the reaction in step (i) disclosed herein is further carried out in the presence of cuprous iodide.

In some embodiments, the reaction in step (i) disclosed herein is carried out by heating. Preferably, the heating refers to heating to 80° C.-90° C. In some embodiments, the reaction in step (i) disclosed herein is carried out at 80° C.-90° C. or 82° C.-90° C. In some embodiments, the reaction in step (i) disclosed herein is carried out at about 80° C., 82° C. or 90° C.

In some embodiments, the solvent 9 disclosed herein is methanol, ethanol, isopropanol, tetrahydrofuran, ethyl acetate, water, or any combination thereof.

In some embodiments, the reductant is Zn, Fe, $SnCl_2$ or a hydrate thereof, $Na_2S$ or a hydrate thereof, a mixture of $Na_2S$ or a hydrate thereof and S, $Na_2S_2$ or a hydrate thereof, $PtO_2$ or Raney nickel. In some embodiments, the reductant disclosed herein is a mixture of $Na_2S$ or a hydrate thereof and S. In some embodiments, the reductant disclosed herein is a mixture of $Na_2S$ or a hydrate thereof and S in a molar ratio of about 1:1. The S disclosed herein is elementary substance S; in some embodiments, the S is sulfur powder.

In some embodiments, the reaction in step (ii) is further carried out in the presence of an acidic reagent, wherein the acidic reagent is HCl, AcOH or $NH_4Cl$.

In some embodiments, the reaction in step (ii) is carried out in the presence of Zn and $NH_4Cl$, or Fe and HCl, or Fe and $NH_4Cl$, or stannous chloride dihydrate and HCl. In some embodiments, the reaction in step (ii) is carried out in the presence of $Na_2S$ or a hydrate thereof, or a mixture of $Na_2S$ (or a hydrate thereof) and elementary substance S; For example, the reaction in step (ii) is carried out in the presence of $Na_2S \cdot 9H_2O$, or a mixture of $Na_2S \cdot 9H_2O$ and elementary substance S.

In some embodiments, the reaction in step (ii) disclosed herein is carried out at room temperature or by heating. Preferably, the heating refers to heating to 65° C.-100° C. In some embodiments, the reaction in step (ii) disclosed herein is carried out by heating, and wherein the heating refers to heating to 65° C.-100° C. In some embodiments, the reaction in step (ii) disclosed herein is carried out at room temperature or 65° C.-100° C. In some embodiments, the reaction in step (ii) disclosed herein is carried out at room temperature, or about 65° C., 70° C., 75° C., 78° C., 80° C., 85° C., 90° C., 95° C. or 100° C.

In some embodiments, the reaction in step (ii) disclosed herein comprises reacting a compound having Formula (VII) in the presence of Zn to give the compound having Formula (VI); furthermore, the reaction can be carried out in the presence of an acidic reagent, wherein the acidic reagent includes but is not limited to ammonium chloride ($NH_4Cl$). In some embodiments, the reaction in step (ii) in the presence of Zn is carried out at room temperature or by heating. In other embodiments, the reaction in step (ii) disclosed herein in the presence of Zn is carried out at room temperature; the reaction condition of reaction in step (ii) carried out at room temperature disclosed herein is mild, suitable for scale-up production, and beneficial to reduce production costs.

In some embodiments, the reaction in step (ii) is carried out by reacting the compound having Formula (VII) in the presence of $Na_2S$ or a hydrate thereof, or a mixture of $Na_2S$ (or a hydrate thereof) and elementary substance S to give the compound having Formula (VI); the $Na_2S$ or a hydrate thereof includes but is not limited to $Na_2S \cdot 9H_2O$. Furthermore, the reaction in step (ii) is carried out by heating, wherein the heating refers to heating to 80° C.-100° C., preferably 80° C., i.e., the reaction in step (ii) is carried out at 80° C.-100° C., preferably 80° C. in the presence of $Na_2S$ or a hydrate thereof, or a mixture of $Na_2S$ (or a hydrate thereof) and elementary substance S. In some embodiments, the solvent 9 used in the reaction in step (ii) in the presence of Na₂S or a hydrate, or a mixture of Na₂S (or a hydrate thereof) and elementary substance S disclosed herein is methanol, ethanol, isopropanol, water, or any combination thereof. Na₂S or a hydrate thereof is used in the reaction in step (ii) as a reductant, makes the waste produced by the reaction less, thus makes the reaction more environmentally friendly, and more suitable for industrial production.

In one aspect, also provided herein is an intermediate compound having Formula (II-a) for preparing the compound represented by Formula (II),

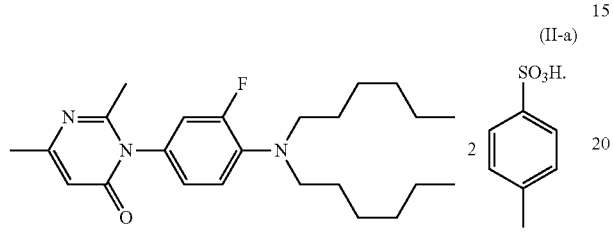
(II-a)

In another aspect, provided herein is an another intermediate compound having Formula (V) for preparing the compound represented by Formula (II),

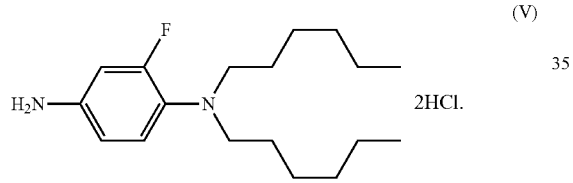
(V)

The salt disclosed herein, for example, the hydrochloride of compound having Formula (I), (II-a) or (V), can be further purified by methods such as triturating, etc. Wherein, the solvent used in the triturating is not limited, including but not limited to, dichloromethane, ethyl acetate, methanol, ethanol, isopropanol, diisopropyl ether, and the like.

In one aspect, provided herein is a method for preparing a compound having Formula (II) comprises:

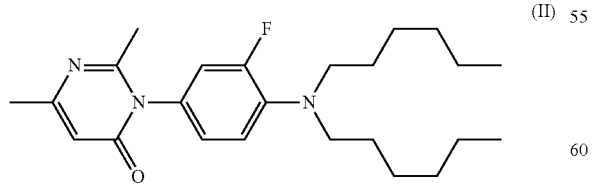
(II)

Step I): reacting 3,4-difluoronitrobenzene with dihexylamine in the presence of base 3 in solvent 8 at about 80° C. to give a compound having Formula (VII);

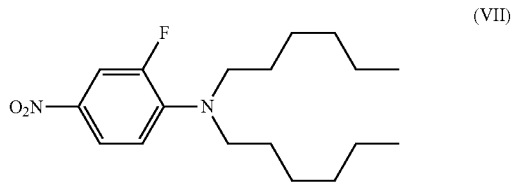
(VII)

wherein, the solvent 8 is N,N-dimethylformamide, toluene, acetonitrile, isopropanol, ethanol, or any combination thereof; the base 3 is lithium hydroxide or a hydrate thereof, sodium carbonate, potassium carbonate, sodium bicarbonate, potassium bicarbonate, potassium phosphate, sodium phosphate, sodium hydroxide, potassium hydroxide, or any combination thereof;

Step II): reacting the compound having Formula (VII) in the present of a reductant in solvent 9 at about 80° C. to give compound having Formula (VI);

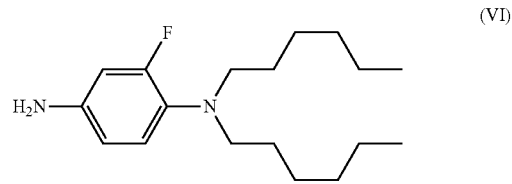
(VI)

wherein, the solvent 9 is methanol, ethanol, isopropanol, water or any combination thereof; the reductant is Na₂S or a hydrate thereof, or a mixture of Na₂S or a hydrate thereof and S;

Step III): reacting a compound having Formula (VI) with a suitable reagent in solvent 7 at room temperature to give the compound having Formula (V)

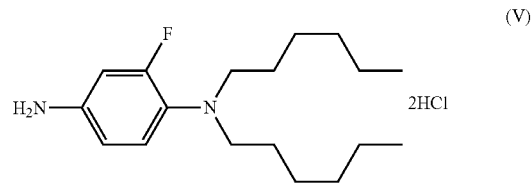
(V)

wherein, the solvent 7 is ethyl acetate, methanol, ethanol, or a combination thereof; the suitable reagent is hydrogen chloride, a hydrogen chloride solution, or Me₃SiCl;

Step IV): reacting a compound having Formula (V) with an acetoacetate in solvent 6 at about 105° C. to about 110° C. to give the compound having Formula (IV),

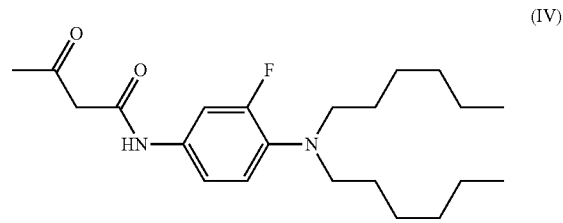 [SMILES: CCCCCCN(CCCCCC)c1ccc(NC(=O)CC(C)=O)cc1F]
(IV)

wherein the solvent 6 is toluene, water, or any combination thereof; the acetoacetate is methyl acetoacetate, ethyl acetoacetate, isopropyl acetoacetate or tert-butyl acetoacetate;

Step V): reacting a compound having Formula (IV) with an ammonium salt in solvent 5 at about 25° C. to about 40° C. to give the compound having Formula (III);

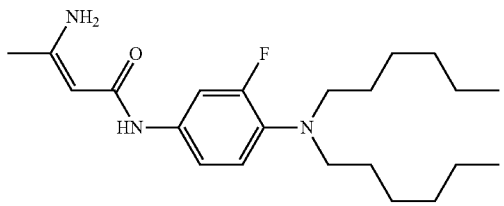
(III)

wherein the solvent 5 is methanol, ethanol, isopropanol, water, or any combination thereof; the ammonium salt is ammonium chloride, ammonium bromide, ammonium acetate, ammonium formate, or ammonium bicarbonate;

Step VI): reacting a compound having Formula (III) with triethyl orthoacetate at 80° C.-140° C., preferably at about 120° C. to give the compound having Formula (II), wherein the amount of triethyl orthoacetate is 2.0 to 4.0 molar equivalents relative to the amount of the compound having Formula (III).

In some embodiments, the reaction of Step IV) may be carried out in the present of base 2 which is triethylamine, N,N-diisopropylethylamine, pyridine, methylmorpholine, potassium carbonate, sodium carbonate, sodium bicarbonate, potassium bicarbonate, or any combination thereof; and the reaction of Step V) may be carried out in the present of base a which is potassium carbonate, sodium carbonate, sodium bicarbonate, potassium bicarbonate, or any combination thereof.

In another aspect, provided herein is a method for preparing a compound having Formula (II) comprising:

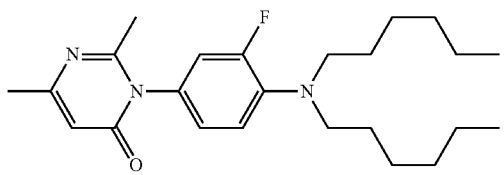
(II)

Step Ia): reacting 3,4-difluoronitrobenzene with dihexylamine in the presence of base 3 in solvent 8 at about 80° C. to give a compound having Formula (VII);

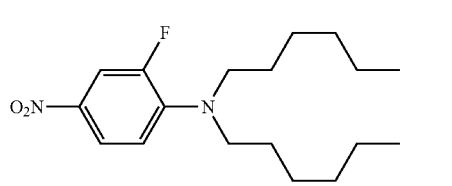
(VII)

wherein, the solvent 8 is N,N-dimethylformamide, toluene, acetonitrile, isopropanol, ethanol, or any combination thereof; the base 3 is lithium hydroxide or a hydrate thereof, sodium carbonate, potassium carbonate, sodium bicarbonate, potassium bicarbonate, potassium phosphate, sodium phosphate, sodium hydroxide, potassium hydroxide, or any combination thereof;

Step IIa): reacting the compound having Formula (VII) in the present of a reductant in solvent 9 at about 80° C. to give compound having Formula (VI);

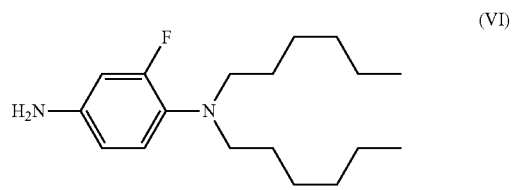
(VI)

wherein, the solvent 9 is methanol, ethanol, isopropanol, water or any combination thereof; the reductant is Zn, Fe, Na$_2$S or a hydrate thereof, a mixture of Na$_2$S or a hydrate thereof and S;

Step IIIa): reacting a compound having Formula (VI) with a suitable reagent in solvent 7 at room temperature to give the compound having Formula (V),

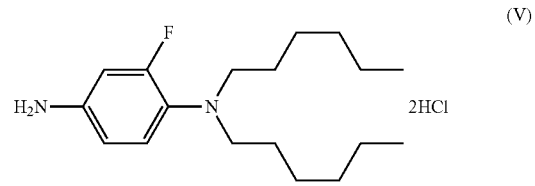
(V)

wherein, the solvent 7 is ethyl acetate, methanol, ethanol, or a combination thereof; the suitable reagent is hydrogen chloride, a hydrogen chloride solution, or Me3SiCl;

Step IVa): reacting a compound having Formula (V) with diketene in the present of base 2 in solvent 6 at room temperature to give the compound having Formula (IV),

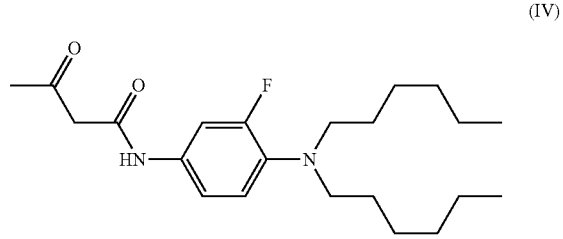 [SMILES: CCCCCCN(CCCCCC)c1ccc(NC(=O)CC(C)=O)cc1F]
(IV)

wherein the solvent 6 is dichloromethane, tetrahydrofuran, toluene, acetone, acetonitrile, water, or any combination thereof; the base 2 is triethylamine, N,N-diisopropylethylamine, potassium carbonate, sodium carbonate, sodium bicarbonate, or potassium bicarbonate;

Step Va): reacting a compound having Formula (IV) with a solution of ammonia in alcohol in solvent 5 at about 40° C. to about 65° C. to give the compound having Formula (III);

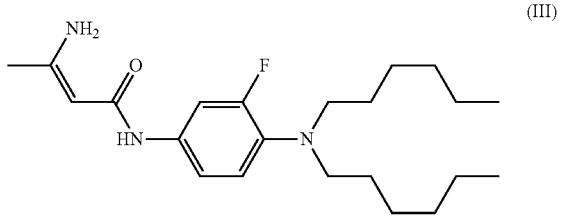 [SMILES: CCCCCCN(CCCCCC)c1ccc(NC(=O)/C=C(/C)N)cc1F]

wherein the solvent 5 is methanol, ethanol, isopropanol, water, or any combination thereof; the solution of ammonia in alcohol is a solution of ammonia in methanol; the amount of ammonia in the solution of ammonia in methanol is 2.0 to 4.0 molar equivalents relative to the amount of the compound having Formula (IV);

Step VIa): reacting a compound having Formula (III) with triethyl orthoacetate at 80° C.-140° C., preferably at about 120° C. to give the compound having Formula (II), wherein the amount of triethyl orthoacetate is 2.0 to 4.0 molar equivalents relative to the amount of the compound having Formula (III).

In some embodiments, the reaction of Step Ia) is further carried out in the presence of cuprous iodide; and the reaction of Step IIa) is further carried out in the presence of an acidic reagent, wherein the acidic reagent is HCl, AcOH or NH4Cl.

In one aspect, provided herein is a method for preparing a compound having Formula (I) comprises:

reacting a compound having Formula (II) prepared by any one of the methods disclosed herein with hydrogen chloride or a hydrogen chloride solution in solvent 3 to give the compound having Formula (I),

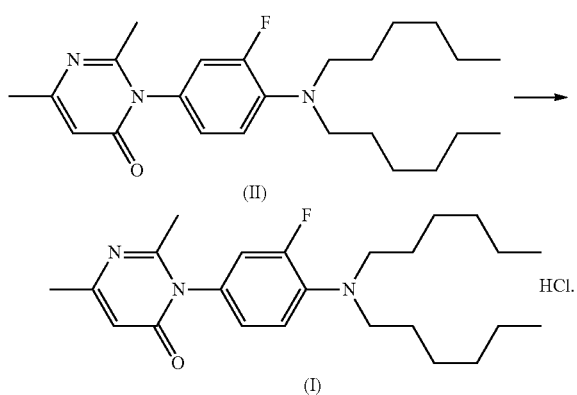

In some embodiments, the solvent 3 disclosed herein is a halogenated hydrocarbon, an ether, a ketone, an ester, an alcohol, toluene, acetonitrile, water, or a combination thereof. In other embodiments, the solvent 3 disclosed herein is dichloromethane, acetonitrile, toluene, methanol, ethanol, isopropanol, 1-propanol, n-butanol, tetrahydrofuran, t-butanol, ethyl acetate, isobutanol, isopentanol, n-propyl acetate, isopropyl acetate, 4-methyl-2-pentanone, dimethyl phthalate, methyl methacrylate, 1,4-dioxane, ethyl formate, xylene, methyl tert-butyl ether, N-methyl pyrrolidone, water, or any combination thereof.

In some embodiments, the hydrogen chloride solution disclosed herein is a solution of hydrogen chloride in water, a solution of hydrogen chloride in ethyl acetate or a solution of hydrogen chloride in isopropanol, or any combination thereof. In some embodiments, the hydrogen chloride solution disclosed herein is 30% solution of hydrogen chloride in isopropanol. In some embodiments, the hydrogen chloride solution disclosed herein is a solution of hydrogen chloride in water, i.e., hydrochloric acid, and the solution of hydrogen chloride in water includes but is not limited to concentrated hydrochloric acid (mass percent is about 37%, and molar concentration is about 12 mol/L), or a hydrochloric acid having a certain concentration (such as a hydrochloric acid having a molar concentration of about 9.8 mol/L or having a mass percent of about 31%). In some embodiments, the hydrogen chloride solution disclosed herein is an industrial hydrochloric acid. In some embodiments, the hydrogen chloride solution disclosed herein is hydrochloric acid having a mass percent of about 30%-33%.

In some embodiments, the reaction disclosed herein for preparing the compound having Formula (I) is carried out at room temperature or by heating. In some embodiments, the heating disclosed herein refers to heating to about 80° C., i.e., the reaction disclosed herein for preparing the compound having Formula (I) is carried out at about 80° C. In some embodiments, the reaction disclosed herein for preparing the compound having Formula (I) is carried out by heating to reflux. It should be understood that the heating to reflux disclosed herein refers to heating to the boiling temperature of the solvent. In some embodiments, the reaction disclosed herein for preparing the compound having Formula (I) is carried out at room temperature.

Preferably, the method for preparing the compound having Formula (I) comprising reacting the compound having Formula (II) with a hydrogen chloride solution in solvent 3 by heating to give the compound having Formula (I), wherein, the solvent 3 includes but is not limited to isopropyl alcohol, ethyl acetate, dichloromethane, methanol, ethanol, tert-butanol, methyl tert-butyl ether, or N-methylpyrrolidone; the hydrogen chloride solution includes but is not limited to a solution of hydrogen chloride in water; and the heating refers to heating to reflux, or heating to about 80° C.

Preferably, the method for preparing the compound having Formula (I) comprising reacting the compound having Formula (II) with a hydrogen chloride solution in solvent 3 at room temperature to give the compound having Formula (I), wherein, the solvent 3 includes but is not limited to dichloromethane; the hydrogen chloride solution includes but is not limited to a solution of hydrogen chloride in ethyl acetate or a solution of hydrogen chloride in isopropanol.

In some embodiments, the intermediate product of each step in the method for preparing the compound having Formula (I) is not purified and used directly in the next step, or is worked-up simply (such as filtration, partition, etc.) without further purification to use in the next step. Intermediate without purification or without further purification may cause a little low total yield, and has little effect on the whole. For example, though each intermediate in the preparation of compound having Formula (I) using compound having Formula (V) as raw material is without purification or without further purification, the total yield of the four-step reaction can reach to 60% above. Using the intermediates directly in the next reaction without purification is more suitable for industrial production.

DEFINITIONS AND GENERAL TERMINOLOGY

As described herein, "room temperature" refers to a temperature from about 10° C. to about 40° C. In some embodiments, "room temperature" refers to a temperature from about 20° C. to about 30° C.; in other embodiments, "room temperature" refers to a temperature of about 20° C., about 22.5° C., about 25° C. or about 27.5° C., etc.

"At room temperature or by heating" in the invention refers to the reaction is carried out at a certain temperature, and the certain temperature is room temperature or a specified temperature reached by heating. For example, the description "the reaction for preparing the compound having Formula (III) from compound having Formula (IV) is carried out at room temperature or by heating" denotes that the reaction is carried out at a certain temperature, and the certain temperature is room temperature or a specified temperature reached by heating; for example, the reaction is carried out at room temperature (such as 20° C.-30° C.) or by heating to 30° C.-65° C., i.e., the reaction is carried out at 20° C.-65° C.

In the context of the present invention, all numbers disclosed herein are approximate values. The value of each number is likely to vary by 1%, 2%, 5%, 7%, 8% or 10%. Therefore, whenever a number having a value N is disclosed, any number having the value N+/−1%, N+/−2%, N+/−3%, N+/−5%, N+/−7%, N+/−8% or N+/−10% is specifically disclosed, wherein "+/−" refers to plus or minus. Whenever a numerical range with a lower limit, DL, and an upper limit, DU, is disclosed, any number falling within the range is specifically disclosed.

The "product content" or "proportion of product" in the present invention refers to the content of the product in the reaction system detected by HPLC after the completion of the reaction.

After the reaction in each step proceeds to a certain extent in the present invention, such as the raw material is consumed more than 70%, more than 80%, more than 90%, more than 95%, or completely by monitoring, the reaction mixture is worked up, such as cooled, collected, extracted, filtered, separated, purified or a combination thereof. The reaction can be monitored by conventional method such as thin-layer chromatography (TLC), high performance liquid chromatography (HPLC), gas chromatography (GC), and the like. The reaction mixture can be worked up by conventional method, for example, the crude product can be collected by concentrating the reaction mixture through vacuum evaporation or conventional distillation and is used directly in the next reaction; or the crude product can be obtained by filtration of the reaction mixture and is used directly in the next operation; or the crude product can be obtained by pouring out the supernatant liquid of the reaction mixture after standing a while and is used directly in the next operation; or the crude product can be purified by extraction of the reaction mixture in a suitable organic solvent or a combination of solvents, distillation of the reaction mixture, cystallization, column chromatography, rinse, or trituration, etc.

The term "about" in the present invention is used to describe a value that can be ranged for 10% from up and down. In some embodiments, the term "about" in the present invention is used to describe a value that can be ranged for 5% from up and down. In some embodiments, the term "about" in the present invention is used to describe a value that can be ranged for 3%, 2% or 1% from up and down. It should be understood that the numerical error range modified by "about" is based on an actual or reasonable error range of the value it describes.

In each step of the reaction described in the present invention, the raw materials or other reagents may be added dropwise to the reaction system. Each dropwise addition and each step of the reaction is carried out at a temperature, and any temperature suitable for each dropwise addition or each step is within the scope of the invention. Additionally, many similar modifications or equivalent alternatives in the art, or temperatures and temperature ranges equivalent to those described herein, are all deemed to be within the scope of the present invention. The present invention provides a preferred temperature or temperature range for each dropwise addition, and a preferred temperature or temperature range for each reaction.

The description "solvent 1", "solvent 2", "base 1" or "base 2", etc. in the present invention uses Arabic numerals 1, 2, 3, . . . behind "solvent" or "base" only to better distinguish the solvent or base used in each step, and the Arabic numbers have no specific meaning. For example, the solvent 1 includes all solvents suitable for the reaction of compound having Formula (II) with p-toluenesulfonic acid or a hydrate thereof, including but not limited to, dichloromethane, acetonitrile, toluene, isopropanol, 1-propanol, n-butanol, tetrahydrofuran, t-butanol, ethyl acetate, isobutanol, isopentanol, n-propyl acetate, isopropyl acetate, 4-methyl-2-pentanone, dimethyl phthalate, methyl methacrylate, 1,4-dioxane, ethyl formate, xylene, water, or any combination thereof.

The solvent used in each reaction step of the invention is not particularly restricted, and any solvent is within the scope of the invention so long as it can dissolve the raw materials to a certain extent and doesn't inhibit the reaction. Additionally, many similar modifications or equivalent alternatives in the art, or any solvent, any combination of solvents and the combination of solvents in different proportions equivalent to those described herein are all deemed to be within the scope of the present invention. The preferred solvents are provided herein for each reaction step.

The product of each reaction step described in the present invention can be purified by recrystallization under a suitable condition. The solvent used for the recrystallization is not particularly restricted, and any solvent is within the scope of the invention so long as it can dissolve the crude product to a certain extent and the crystal product can be precipitated out under a certain condition. Additionally, many similar modifications or equivalent alternatives in the art, or any solvent, any combination of solvents and the combination of solvents in different proportions equivalent to those described herein are all deemed to be within the scope of the present invention. Wherein the solvent could be alcohols, ethers, alkanes, halohydrocarbons, esters, ketones, aromatic hydrocarbons, acetonitrile, acetic acid, water, N,N-dimethyl formamide (DMF), or a combination thereof. Such as water, acetic acid, methanol, ethanol, n-propanol, i-propanol, n-butanol, i-butanol, tert-butanol, petroleum ether, n-pentane, n-hexane, n-heptane, cyclohexane, DMF, tetrahydrofuran, ethyl ether, isopropyl ether, dioxane, methyl tertiary butyl ether, dimethoxylethane, diethylene glycol dimethyl ether, triethylene glycol dimethyl ether, dichloromethane, 1,2-dichloroethane, chloroform, tetrachloromethane, ethyl acetate, isopropyl acetate, acetone, butanone, benzene, toluene, xylene or a combination thereof.

The content of water in the solvent is not particularly restricted, that is, the content of water in the solvent does not affect the occurrence of the reaction of the present invention. So long as the solvent containing a certain amount of water can be used in the reaction disclosed herein, it is deemed to be within the scope of the present invention. The content of water in the solvent is approximately less than 0.05%, less than 0.1%, less than 0.2%, less than 0.5%, less than 5%, less than 10%, less than 25%, less than 30%, or 0%. In some embodiments, the content of water in the solvent within a certain range is more conducive to the reaction; for example, in the step of using ethanol as a reaction solvent, anhydrous ethanol is more favorable for the reaction. In some embodiments, the content of water in the solvent beyond a certain range may affect the progress of the reaction (for example, affect the yield of the reaction), but does not affect the occurrence of the reaction.

GENERAL SYNTHETIC PROCEDURES

In the present invention, if the chemical name of the compound doesn't match the corresponding structure, the compound is preferentially characterized by the corresponding structure.

In the examples described below, unless otherwise indicated all temperatures are set forth in degrees Celsius (° C.). Reagents were purchased from commercial suppliers such Aladdin Reagents (shanghai) Co., Ltd, LinkChem Co., Ltd, Shanghai Demo Medical Tech Co., Ltd, Beijing Ouhe Technology Co., Ltd, and were used without further purification unless otherwise indicated. Common solvents were purchased from commercial suppliers such as Chengdu Kelong Chemical Reagent Factory, Zhejiang Huabang Medical & Chemical Co., Ltd., Sichuan Weibo Technology Development Co., Ltd., and Zhejiang Bulk Chemical Co., LTD.

$^1$H NMR spectra were recorded by a Bruker Avance 400 MHz spectrometer or Bruker Avance III HD 600 spectrometer, using $CDCl_3$, $d_6$-DMSO, $CD_3OD$, $D_2O$ or $d_6$-acetone (reported in ppm) as solvent, and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets), td (triplet of doublets), ddd (doublet of doublet of doublets), ddt (doublet of doublet of triplets), dddd (doublet of doublet of doublet of doublets). Coupling constants, when given, were reported by J in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used in the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were shown in Table 1.

TABLE 1

The gradient condition of the mobile phase in Low-resolution mass spectrum analysis

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

The purity of the compound was evaluated by Agilent 1260 High Performance Liquid Chromatography (HPLC). Wherein, the HPLC instrument was equipped with a G1311B quaternary pump, a G1329B autosampler, a G1316A TCC (column temperature was maintained at 35° C.), and a G1315D DAD detector. The column was an Agilent Zorbax Extend C18 (size 4.6×150 mm, 5 μm); the flow rate was 1.0 mL/min; the detection wavelength was 250 nm; the mobile phase and gradient elution conditions were shown in Tables 2-5.

TABLE 2

The mobile phase and gradient condition 1 in HPLC analysis

| Time(min) | A (acetonitrile) | B ($H_2O$) |
|---|---|---|
| 0-10 | 30-90 | 70-10 |
| 10-25 | 90 | 10 |
| 25-26 | 10 | 90 |
| 26-31 | 90 | 10 |

TABLE 3

The mobile phase and gradient condition 2 in HPLC analysis

| Time (min) | A (acetonitrile) | B ($H_2O$) |
|---|---|---|
| 0-10 | 10-30 | 90-70 |
| 10-15 | 30-90 | 70-10 |
| 15-20 | 90 | 10 |
| 20-21 | 10 | 90 |
| 21-26 | 10 | 90 |

TABLE 4

The mobile phase and gradient condition 3 in HPLC analysis

| Time (min) | A (acetonitrile) | B ($H_2O$) |
|---|---|---|
| 0-15 | 10-90 | 90-10 |
| 15-25 | 90 | 10 |
| 25-26 | 10 | 90 |
| 26-31 | 10 | 90 |

TABLE 5

The mobile phase and gradient condition 4 in HPLC analysis

| Time (min) | A (acetonitrile) | B (0.05% ammonium hydroxide (pH 8.0)) |
|---|---|---|
| 0-8 | 10-25 | 90-75 |
| 8-15 | 25-75 | 75-25 |
| 15-20 | 75 | 25 |
| 20-21 | 10 | 90 |
| 21-26 | 10 | 90 |

The following abbreviations are used throughout the specification:

| | | | |
|---|---|---|---|
| CDCl$_3$ | deuterated chloroform | K$_2$CO$_3$ | potassium carbonate |
| D$_2$O | deuteroxide | | |
| DMSO | dimethylsulfoxide | K$_3$PO$_4$ | potassium phosphate |
| DMSO-d$_6$ | deuterated dimethyl sulfoxide | KOH | potassium hydroxide |
| CuI | cuprous iodide | | |
| HCl | hydrogen chloride | LiOH•H$_2$O | lithium hydroxide monohydrate |
| Me$_3$SiCl | trimethylchlorosilane | | |
| PTSA | p-toluenesulfonic acid | THF | tetrahydrofuran |
| MeC(OEt)$_3$ | triethyl orthoacetate | DCM | dichloromethane |
| DIPEA | N,N-diisopropylethylamine | kg | kilogram |
| DMF | N,N-dimethylformamide | g | gram |
| IPA | isopropanol | mg | milligram |
| MeCN | acetonitrile | mol | mole |
| TLC | thin layer chromatography | mmol | millimole |
| HPLC | high performance liquid chromatography | L | liter |
| | | mL | milliliter |
| equiv | the abbreviation of equivalent, chemical equivalent | | |

The following scheme describes the method for preparing the compound having Formula (I) or (II).

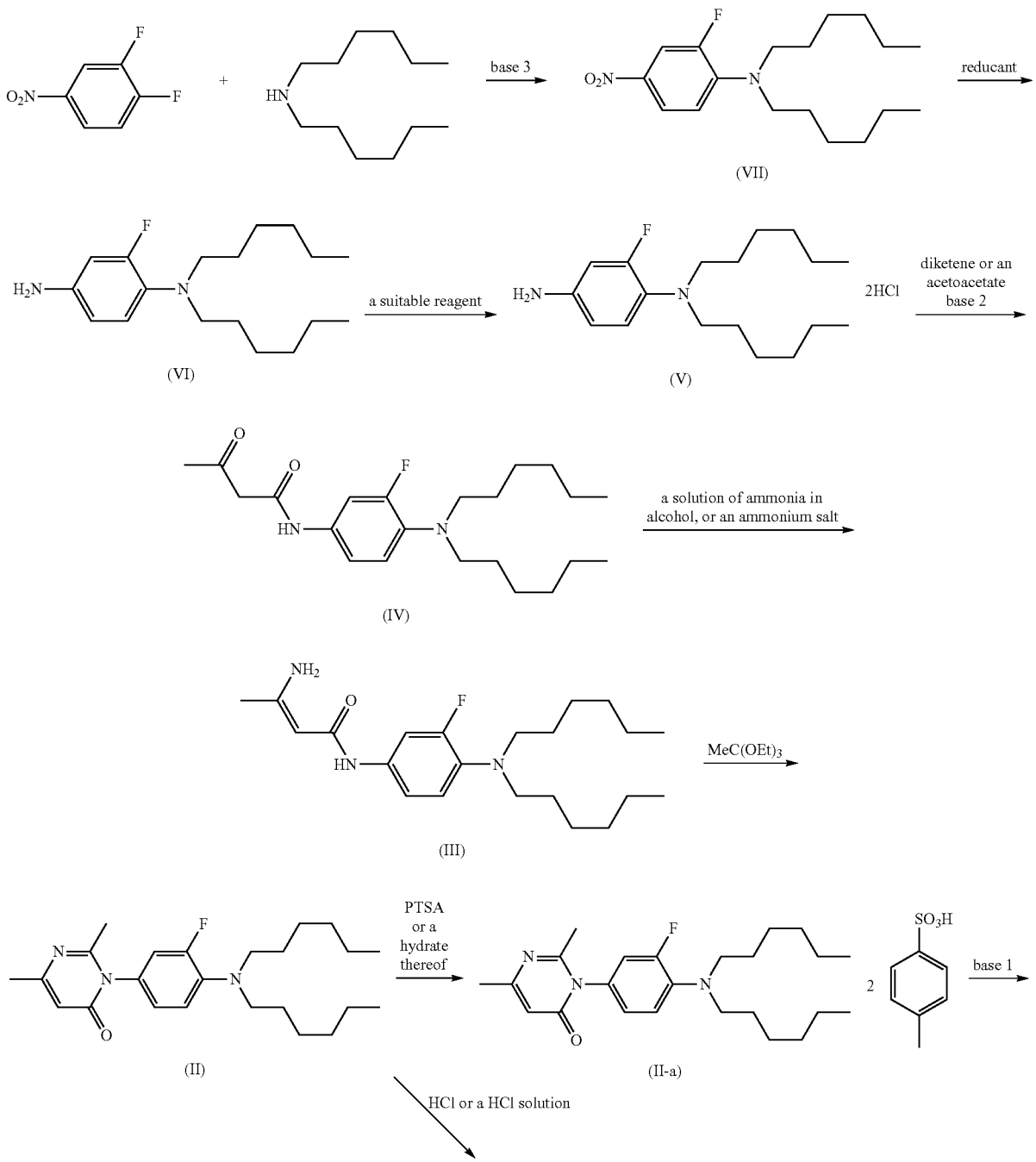

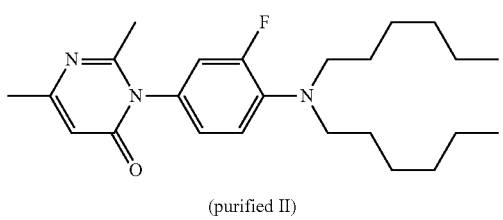 (purified II)

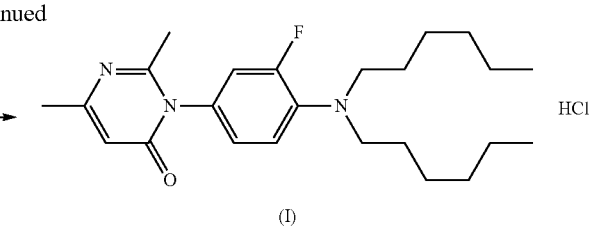 (I)

The compound having Formula (I) or (II) can be prepared by the method above: 3,4-difluoronitrobenzene can react with dihexylamine in the presence of base 3 (such as lithium hydroxide, sodium carbonate, sodium hydroxide, potassium hydroxide, triethylamine, pyridine, and the like) to give a 4-substituted nitrobenzene compound having Formula (VII), then the compound having Formula (VII) can react in the presence of a reductant (such as a combination of a metal catalyst and an acidic reagent (such as $Zn/NH_4Cl$, Fe/HCl, etc.), or a reductant containing sulfur (such as $Na_2S_2$ or a hydrate thereof, $Na_2S$ or a hydrate thereof, or a mixture of $Na_2S$ (or a hydrate thereof) and S), etc.) to give an aniline compound having Formula (VI), and then the compound having Formula (VI) can react with a suitable reagent (such as HCl or a solution thereof, $Me_3SiCl$ or $SOCl_2$, etc.) to give a compound having Formula (V). The compound having Formula (V) can react with diketene or an acetoacetate in the presence of base 2 (e.g., triethylamine, N,N-diisopropylethylamine, pyridine, methylmorpholine, potassium carbonate, sodium carbonate, sodium hydroxide, potassium hydroxide, lithium hydroxide, sodium bicarbonate, potassium bicarbonate, etc., or any combination thereof) to give a compound having Formula (IV), and the compound having Formula (IV) can firstly reacts with a solution of ammonia in alcohol or a ammonium salt to give a compound having Formula (III), and then the compound having Formula (III) can react with triethyl orthoacetate to give a pyrimidinone compound having Formula (II). The compound having Formula (II) can directly react with HCl or a solution thereof to give the hydrochloride compound having Formula (I), or also can be purified by acidifying (e.g., by reacting with p-toluenesulfonic acid or a hydrate thereof, etc) and alkalizing (such as by adding sodium hydroxide, sodium carbonate, potassium carbonate or lithium hydroxide, etc.) in sequence, and then react with HCl or a solution thereof to give the hydrochloride having Formula (I).

DESCRIPTION OF THE PREFERRED EMBODIMENTS

The examples of the present invention disclose a method for preparing a pyrimidinone compound having Formula (I) or (II). Skilled in the art can learn from this article to properly improve the process parameters to implement the preparation. Of particular noted is that all similar replacements and modifications are apparent to the skilled person, and they are deemed to be included in the present invention. The method of the present invention has been described by preferred Examples. And skilled person can clearly achieve and apply the techniques disclosed herein by making some changes, appropriate alterations or combinations to the methods of the invention without departing from spirit, principles and scope of the present disclosure.

In order to make the present invention to be better understood, it is detailed below through examples.

EXAMPLES

Example 1
2-fluoro-N,N-dihexyl-4-nitrophenylamine

Method One:

Embodiments 1-4

To a solvent (50 mL) were added 3,4-difluoronitrobenzene (4.77 g, 30 mmol), di-n-hexane (5.84 g, 31.5 mmol), base (60 mmol) and cuprous iodide (0.285 g, 1.5 mmol). The mixture was heated and stirred overnight. After the reaction was completed, a sample of the reaction mixture was taken and detected by HPLC, and the reaction mixture was cooled to room temperature, filtered and evaporated to give yellow liquid. The reaction temperatures, the solvents and the bases used in Embodiments 1-4 were shown in table A.

TABLE A

| Embodiment | Solvent | Reaction temperature | Base | Content of the product |
|---|---|---|---|---|
| Embodiment 1 | Acetonitrile | 82° C. | Potassium carbonate | 92.63% |
| Embodiment 2 | Acetonitrile | 82° C. | Potassium phosphate | 92.80% |
| Embodiment 3 | Acetonitrile | 90° C. | Lithium hydroxide monohydrate | 97.48% |
| Embodiment 4 | N,N-Dimethylformamide | 90° C. | Potassium phosphate | 92.73% |
| Embodiment 5 | Acetonitrile | 90° C. | Potassium hydroxide | 72.65% |
| Embodiment 6 | N,N-Dimethylformamide | 90° C. | Potassium hydroxide | 55.60% |

Method Two:

To a 1000 mL single-neck flask were added lithium hydroxide monohydrate (28.00 g, 667.3 mmol), 3,4-difluoronitrobenzene (50.00 g, 314.3 mmol), di-n-hexylamine (70.00 g, 377.7 mmol) and acetonitrile (400.0 g). The mixture was heated to 80° C. and refluxed under nitrogen protection. After the reaction was completed, the reaction mixture was cooled to about 25° C., and stirred at this temperature for 2 hours, then filtered by suction. The filtrate was distilled under reduced pressure, and the concentrated residue was dissolved in ethyl acetate (400.0 g) uniformly by stirring, then the mixture was washed with saturated aqueous ammonium chloride (400 mL) and water (400 mL×2). The organic layer was distilled under reduced pressure to give yellow liquid which was used directly in the next reaction without further treatment.

Example 2 2-fluoro-$N^1,N^1$-dihexylbenzene-1,4-diamine

Method One:

Embodiments 1-3

To a 100 mL round bottom flask were added water (10 mL) and concentrated hydrochloric acid (2.0 mL), then iron powder (3.35 g, 60.0 mmol) was added in one time. The mixture was stirred and heated to 65° C. to activate the iron powder for 50 minutes, then the aqueous layer was poured and abandoned. 2-Fluoro-N,N-dihexyl-4-nitrophenylamine (3.24 g, 10.0 mmol) was dissolved in a solvent, and the obtained solution was added into the iron powder. The resulting mixture was adjusted with hydrochloric acid to pH 2, and then heated overnight. After the reaction was completed, the mixture was cooled to room temperature and adjusted with triethylamine to basicity. The mixture was filtered, and concentrated in vacuo to remove the solvent. To the residue was added water (50 mL), and the mixture was extracted with ethyl acetate (100 mL×2). The combined organic layers were washed with saturated brine (80 mL×2), dried over anhydrous sodium sulfate and concentrated in vacuo to remove the solvent and give brown liquid. The activation conditions of the iron powder, the reaction solvents, the reaction temperatures, and the experimental results in Embodiments 1-3 were shown in Table B.

TABLE B

| Embodiment | The activation condition of the iron powder | Reaction solvent | Reaction temperature | Yield |
|---|---|---|---|---|
| Embodiment 1 | Heating to 65° C. and activating for 50 minutes | Methanol (10 mL) and tetrahydrofuran (20 mL) | 65° C. | 93.4% |
| Embodiment 2 | Heating to 70° C. and activating for 1 hour | Methanol (30 mL) | 70° C. | 90.1% |
| Embodiment 3 | Heating to 70° C. and activating for 1 hour | Ethanol (30 mL) | 70° C. | 98.0% |

Method Two:

To a 100 mL round bottom flask were added water (10 mL) and concentrated hydrochloric acid (2.0 mL), then iron powder (1.96 g, 35.0 mmol) was added in one time. The mixture was stirred and heated to 100° C. to activate the iron powder for 1 hour, then the aqueous layer was poured and abandoned. A solution of 2-fluoro-N,N-dihexyl-4-nitrophenylamine (3.24 g, 10.0 mmol) in ethanol (30 mL) and ammonium chloride (5.35 g, 100 mmol) were added into the iron powder. The resulting mixture was adjusted with hydrochloric acid to pH 2, and then heated to 100° C. and stirred overnight. After the reaction was completed, the mixture was filtered, and the filtrate was evaporated in vacuo to remove the solvent. To the residue was added water (50 mL), and the mixture was extracted with ethyl acetate (100 mL×2). The combined organic layers were washed with saturated brine (80 mL×2), dried over anhydrous sodium sulfate and concentrated in vacuo to remove the solvent and give brown liquid (2.80 g, 95.2%).

Method Three:

To a 100 mL round bottom flask were added 2-fluoro-N,N-dihexyl-4-nitrophenylamine (3.24 g, 10.0 mmol) and ethanol (30 mL). The mixture was stirred at room temperature, then stannous chloride dihydrate (9.026 g, 40.0 mmol) was added in portions. After addition, the mixture was heated to 85° C. and stirred for 4.5 hours. After the reaction was completed, the mixture was cooled to room temperature, and evaporated in vacuo to remove the solvent. To the residue were added water (50 mL) and ethyl acetate (50 mL), and the mixture was adjusted with saturated aqueous sodium bicarbonate solution to pH 7. The mixture was filtered, and the filtrate was extracted with ethyl acetate (100 mL×2). The combined organic layers were washed with saturated brine (60 mL×2), dried over anhydrous sodium sulfate and concentrated in vacuo to remove the solvent and give brown liquid (2.74 g, 93.2%).

Method Four:

To a 100 mL round bottom flask were added 2-fluoro-N,N-dihexyl-4-nitrophenylamine (3.24 g, 10.0 mmol) and ethyl acetate (30 mL). The mixture was stirred at room temperature, then stannous chloride dihydrate (9.026 g, 40.0 mmol) was added in portions. After addition, to the mixture was added dropwise concentrated hydrochloric acid (2.5 mL, 30 mmol), then the mixture was heated to 75° C. and stirred overnight. After the reaction was completed, the mixture was cooled to room temperature, and the mixture was adjusted with saturated aqueous sodium bicarbonate to pH 7. The mixture was filtered, and the filtrate was extracted with ethyl acetate (100 mL×2). The combined organic layers were washed with saturated brine (60 mL×2), dried over anhydrous sodium sulfate and concentrated in vacuo to remove the solvent and give brown liquid (2.83 g, 96.3%).

Method Five:

To a 100 mL round bottom flask were added 2-fluoro-N,N-dihexyl-4-nitrophenylamine (3.24 g, 10.0 mmol) and ethanol (25 mL). The mixture was stirred at room temperature, and a solution of sodium sulfide nonahydrate (3.60 g, 15.0 mmol) in water (20 mL) was added. After the addition, the mixture was heated to 100° C. and stirred for 13 hours. After the reaction was completed, the mixture was cooled to room temperature and adjusted with saturated aqueous sodium bicarbonate to pH 7. The mixture was filtered, and the filtrate was concentrated to remove the solvent. To the residue were added water (50 mL) and ethyl acetate (50 mL). The mixture was extracted with ethyl acetate (100 mL×2). The combined organic layers were washed with saturated brine (60 mL×2), dried over anhydrous sodium sulfate and concentrated to remove the solvent and give brown liquid (2.88 g, 98.0%).

Method Six:

Embodiment 1

To a 100 mL single-neck flask were added sodium sulfide nonahydrate (18.5 g, 77.0 mmol), sulfur (2.48 g, 77.4 mmol) and $H_2O$ (10 mL). The mixture was heated to 80° C. and stirred to the solid was dissolved completely, then cooled to 40° C. To the reaction mixture was added a solution of 2-fluoro-N,N-dihexyl-4-nitrophenylamine (5.00 g, 15.0 mmol) in ethanol (30 mL). The mixture was heated to 80° C. and stirred for 5 hours. The mixture was cooled to room temperature, and evaporated under reduced pressure to remove the organic solvent. To the residue was added ethyl acetate (20 mL), then the mixture was stirred for 10 minutes and then stood for partition. The organic layer was washed with water (20 mL), and then evaporated under reduced pressure to remove the solvent and give yellow oil (4.25 g, 93.73%).

Embodiment 2

To a 2000 mL single-neck flask were added water (204 g), sodium sulfide nonahydrate (377.00 g, 1550 mmol) and sulphur powder (51.00 g, 1590.5 mmol), then the mixture was heated to 80° C. and stirred until the solid was dissolved completely. The mixture was cooled to 45° C., and degassed and filled with nitrogen, then kept under nitrogen protection. To the reaction mixture was added a solution of 2-fluoro-N,N-dihexyl-4-nitrophenylamine (102.0 g, 314.4 mmol) in ethanol (360 g) prepared from Method Two of Example 1. After the addition, the mixture was heated to 80° C. and stirred. The reaction was completed through monitoring by HPLC, and the mixture was cooled to room temperature, and evaporated under reduced pressure to remove the ethanol. To the concentrated residue was added ethyl acetate (500 g), and the mixture was stirred until the residue was dissolved completely. The mixture was stood and then aqueous layer was partitioned. The organic layers were washed with water (500 mL×2) and saturated aqueous sodium chloride solution (500 mL), and the obtained solution was used directly in the next step.

Method Seven:

Embodiments 1-2

To a 100 mL round bottom flask were added 2-fluoro-N,N-dihexyl-4-nitrophenylamine (3.00 g, 9.25 mmol) and solvent (25 mL), the mixture was stirred at room temperature and then zinc powder (6.05 g, 92.4 mmol) and ammonium chloride (4.95 g, 92.4 mmol) were added. The resulting mixture was stirred at room temperature and the reaction was completed through monitoring by TLC. After posttreatment, brown liquid was obtained. The reaction solvents, reaction times, post-treatment methods of the reactions in Embodiment s1-2 were shown in table C.

TABLE C

| Embodiment | Solvent | Reaction time | Post-treatment method | Yield |
|---|---|---|---|---|
| Embodiment 1 | Ethyl acetate | 17 hours | The reaction mixture was filtered, and the filtrate was washed with water (50 mL) and saturated brine (50 mL), then evaporated under reduced pressure to remove the solvent. | 95.2% |
| Embodiment 2 | Ethanol | 5.5 hours | The reaction mixture was filtered, and the filtrate was evaporated under reduced pressure to remove the solvent. The residue was dissolved in ethyl acetate (50 mL), and the resulting mixture was washed with water (50 mL × 2) and saturated brine (50 mL), then evaporated under reduced pressure to remove the solvent. | 95.2% |

Example 3 2-Fluoro-$N^1$,$N^1$-dihexylbenzene-1,4-diamine Hydrochloride

Method One:

To a 100 mL round bottom flask were added 2-fluoro-$N^1$,$N^1$-dihexylbenzene-1,4-diamine (2.72 g, 9.24 mmol) and ethyl acetate (20 mL). The mixture was stirred, and methanol (1.5 mL, 37 mmol) was added into the mixture, then trimethylchlorosilane (3.1 g, 28 mmol) was added dropwise into the mixture. After addition, the mixture was stirred at room temperature overnight, and then filtered to give an off-white solid (2.74 g, 80.7%).

Method Two:

To a 100 mL round bottom flask were added 2-fluoro-$N^1$,$N^1$-dihexylbenzene-1,4-diamine (5.00 g, 17.0 mmol) and ethyl acetate (40 g). The mixture was stirred, and hydrochloric acid (3.91 mL, 39.1 mmol) was added dropwise into the mixture. The mixture was stirred at room temperature for 5 hours, and filtered. The filter cake was triturated with ethyl acetate (25 g), and then the mixture was filtered by suction. The filter cake was dried at 50° C. in oven to give an off-white solid (4.92 g, 79.0%).

Method Three:

To a solution of 2-fluoro-$N^1$,$N^1$-dihexylbenzene-1,4-diamine in ethyl acetate prepared from Embodiment 2 of Method Six in Example 2 which was placed in a 1000 mL single-neck flask was added anhydrous ethanol (36.1 g, 784 mmol). The mixture was degassed and filled with nitrogen, then protected in nitrogen atmosphere. To the reaction mixture was added dropwise trimethylchlorosilane (85.7 g, 781 mmol). After the addition, the mixture was stirred at room temperature and monitored by TLC until the reaction material was disappeared, then the reaction was stopped. The mixture was filtered, and the filer cake was washed with ethyl acetate (200 g). Then the filter cake was triturated with ethyl acetate (200 g) for 5 hours, and the mixture was filtered. The filter cake was washed with ethyl acetate (200 g), and dried at 60° C. for 8 hours to give a light yellow solid (115.5 g, 92.6%).

Example 4: N-(4-(dihexylamino)-3-fluorophenyl)-3-oxobutanamide

Method One:

To dichloromethane (10 mL) were added 2-fluoro-$N^1$,$N^1$-dihexylbenzene-1,4-diamine hydrochloride (1.5 g, 5.1 mmol) and diketene (640 mg, 7.6 mmol). The mixture was stirred at room temperature, and triethylamine (1.10 g, 11 mmol) was added dropwise into the mixture. After the addition, the mixture was heated to 42° C. and refluxed for 12 hours. The reaction was completed, and quenched with water (30 mL). The aqueous layer was partitioned, and the organic layer was evaporated to dryness under reduced pressure and give black oil (1.80 g, 93.4%).

Method Two:

To dichloromethane (200 mL) were added 2-fluoro-$N^1$,$N^1$-dihexylbenzene-1,4-diamine hydrochloride (30.00 g, 81.65 mmol) and diketene (6.87 g, 81.7 mmol). The mixture was cooled in an ice-bath, and then triethylamine (26 mL, 187.8 mmol) was added dropwise at a temperature of not more than 5° C. The mixture was stirred under the ice-bath condition for 1.5 hours, and then washed with water (200 mL×2) and saturated brine (200 mL). The organic layer was evaporated to dryness under reduced pressure and give black oil (30.00 g, 97.1%).

Method Three:

Embodiments 1-4

2-Fluoro-$N^1$,$N^1$-dihexylbenzene-1,4-diamine hydrochloride was added into a solvent, then the mixture was stirred at room temperature, and a base was added into the mixture. To the mixture was added dropwise diketene, and the temperature of the reaction mixture was controlled below the boiling temperature of the solvent used. After addition, the reaction mixture was stirred and heated naturally to reflux, then cooled naturally to room temperature and stirred at room temperature. The reaction was completed, and a sample of reaction mixture was taken and detected by HPLC. The reaction was quenched with water (30 mL). The aqueous layer was partitioned, and the organic layer was evaporated to dryness under reduced pressure and give black oil. The specific reaction conditions and results in Embodiments 1-4 were as shown in table D.

TABLE D

| Embodiment | Hydrochloride | Diketene | Base/amount | Solvent/amount | Reaction time at room temperature | Content of the product |
|---|---|---|---|---|---|---|
| Embodiment 1 | 30 g | 1.0 equiv | Triethylamine/ 23 mL | DCM/ 200 mL | 0 | 93.06% |
| Embodiment 2 | 1.5 g | 1.2 equiv | Saturated aqueous sodium bicarbonate solution/ 20 mL | THF/ 20 mL | 3 hours | 94.21% |
| Embodiment 3 | 1.5 g | 1.2 equiv | Saturated aqueous sodium bicarbonate solution/ 20 mL | Acetone/ 8 mL | 5 hours | 93.86% |
| Embodiment 4 | 30 g | 2.0 equiv | Saturated aqueous sodium bicarbonate solution/ 60 mL | Acetone/ 150 mL | 1 hour | 95.86% |

Method Four:

2-Fluoro-$N^1$,$N^1$-dihexylbenzene-1,4-diamine hydrochloride (2.03 g, 5.53 mmol) was added into toluene (20 g), then the mixture was stirred at room temperature, and a solution of sodium carbonate (1.33 g, 12.5 mmol) in water (15.0 g) was added into the mixture. The mixture was stirred at room temperature until the solid was dissolved completely, and then stood for partition. The aqueous layer was partitioned, and the organic layer was washed with water (50 mL×2). To the organic layer were added methyl acetoacetate (1.00 g, 8.61 mmol) and DIPEA (0.20 g, 1.5 mmol). The mixture was stirred at 105° C. for 24 hours under nitrogen protection. The reaction mixture was cooled to room temperature and washed with water (50 mL), then evaporated under reduced pressure to give brown oil (1.97 g, 94.2%).

Method Five:

2-Fluoro-$N^1$,$N^1$-dihexylbenzene-1,4-diamine hydrochloride (3.00 g, 8.17 mmol) was added into toluene (30 g), then the mixture was stirred at room temperature, and a solution of sodium carbonate (1.95 g, 18.4 mmol) in water (20.0 g) was added into the mixture. The mixture was stirred at room temperature until the solid was dissolved completely, and then stood for partition. The aqueous layer was partitioned, and the organic layer was washed with water (50 mL×2). To the organic layer were added tert-buyl acetoacetate (3.97 g, 24.6 mmol) and DIPEA (0.32 g, 2.5 mmol). The mixture was stirred at 105° C. for 16 hours under nitrogen protection. The reaction mixture was cooled to room temperature and washed with water (50 mL), then evaporated under reduced pressure to give brown oil (3.06 g, 99.0%).

Method Six:

Embodiments 1-7

2-Fluoro-$N^1$,$N^1$-dihexylbenzene-1,4-diamine hydrochloride was added into toluene (10 g/g), then the mixture was stirred at room temperature, and a solution of sodium carbonate (0.65 g/g) in water (6.5 g/g) was added into the mixture. The mixture was stirred at room temperature until the solid was dissolved completely, and then stood for partition. The aqueous layer was partitioned, and the organic layer was washed with water (20 g/g×2). To the organic layer were added tert-butyl acetoacetate (1.30 g/g) and base (0.10 g/g). The mixture was heated to a certain temperature and stirred under nitrogen protection. The reaction was completed, and the reaction mixture was washed with water (20 g/g), then evaporated under reduced pressure to give brown oil. The amount of the each reagent described in Embodiments 1-7 was based on the ratio of the amount of the reagent to 2-fluoro-$N^1$,$N^1$-dihexylbenzene-1,4-diamine hydrochloride, i.e., the amount of 2-fluoro-$N^1$,$N^1$-dihexylbenzene-1,4-diamine hydrochloride was benchmark when the amount of each reagent was calculated. The reaction temperatures, the reaction times and the bases used in Embodiments 1-7 were as shown in table E.

TABLE E

| Embodiment | Base | Reaction temperature | Reaction time | Yield |
|---|---|---|---|---|
| Embodiment 1 | Triethylamine | 105° C. | 4 hours | 96.96% |
| Embodiment 2 | Pyridine | 105° C. | 4 hours | 96.98% |
| Embodiment 3 | DIPEA | 105° C. | 4 hours | 97.63% |
| Embodiment 4 | Methylmorpholine | 105° C. | 4 hours | 96.72% |
| Embodiment 5 | N/A[*1] | 105° C. | 4 hours | 99.3% |
| Embodiment 6[*2] | N/A | 110° C. | 1 hour | 98.5% |
| Embodiment 7[*2] | N/A | 105° C. | 2 hours | 97.1% |

Notes:
[*1]"N/A" denotes that base was not added in the embodiment;
[*2]the ratios of the amounts of tert-butyl acetoacetate used in Embodiment 6 and Embodiment 7 to the amount of 2-fluoro-$N^1$,$N^1$-dihexylbenzene-1,4-diamine hydrochloride are independently 1.75 g/g and 0.66 g/g.

Embodiment 8

To a 1000 mL single-neck flask were added toluene (500 g) and 2-fluoro-$N^1$,$N^1$-dihexylbenzene-1,4-diamine hydrochloride (50.00 g, 136.1 mmol) prepared from Method Three of Example 3. The mixture was stirred for 15 minutes, then aqueous sodium carbonate (30.0 g) solution was added into the mixture. After addition, the mixture was stirred until the solid was dissolved completely, and then stood for partition. The aqueous layer was partitioned, and the organic layer was washed with water (500 mL×2). To the organic layer was added tert-butyl acetoacetate (32.5 g). The reaction mixture was stirred in nitrogen atmosphere for 30 minutes, then heated to 105° C. and refluxed. The reaction was completed through monitoring by HPLC, then cooled to room temperature, washed with water (500 mL×2), and evaporated under reduced pressure to give light brown liquid, which was used directly in the next step without further purification.

Example 5: (Z)-3-amino-N-(4-(dihexylamino)-3-fluorophenyl)but-2-enamide

Method One:

Embodiments 1-5

N-(4-(Dihexylamino)-3-fluorophenyl)-3-oxobutanamide (500 mg, 1.39 mmol) was dissolved in methanol (10 mL), then a solution of ammonia in methanol (7 mol/L) was added into the mixture. The resulting mixture was stirred at a certain temperature. After the reaction was completed, a sample of reaction mixture was taken for HPLC detection. The reaction mixture was concentrated in vacuo to give brown black liquid. The reaction temperatures, reaction times, the amounts of a solution of ammonia in methanol and the results of Embodiments 1-5 were shown in table F.

TABLE F

| Embodiment | A solution of ammonia in methanol | Reaction temperature | Reaction time | Proportion of product |
| --- | --- | --- | --- | --- |
| Embodiment 1 | 2.0 equiv | 20° C. | 21 hours | 91.4% |
| Embodiment 2 | 3.0 equiv | 20° C. | 21 hours | 92.5% |
| Embodiment 3 | 4.0 equiv | 20° C. | 21 hours | 94.9% |
| Embodiment 4 | 4.0 equiv | 40° C. | 6 hours | 94.2% |
| Embodiment 5 | 4.0 equiv | 65° C. | 6 hours | 93.6% |

Method Two:

Embodiments 1-2

To a 100 mL single-neck flask were added ethanol, N-(4-(dihexylamino)-3-fluorophenyl)-3-oxobutanamide (4.99 g, 13.2 mmol), ammonium acetate (8.16 g, 106 mmol) and sodium carbonate. The mixture was stirred at 25° C. The reaction was completed through monitoring by HPLC, and the reaction mixture was concentrated. The residue was dissolved in dichloromethane (100 mL), and the mixture was washed with water (100 mL×3) and saturated brine (100 mL). The organic layer was concentrated in vacuo to remove the solvent and give brown oil. The amounts of ethanol and sodium carbonate, reaction times and results in Embodiments 1-2 were as shown in table G.

TABLE G

| Embodiment | Ethanol | Sodium carbonate | Reaction time | Yield |
| --- | --- | --- | --- | --- |
| Embodiment 1 | 20 g | N/A | 24 hours | 95.0% |
| Embodiment 2 | 25 g | 8.88 g | 20 hours | 96.2% |

Note:
N/A denotes that sodium carbonate was not added into the reaction mixture of the Embodiment.

Method Three:

Embodiments 1-2

To a 100 mL single-neck flask were added ethanol (15 g), N-(4-(dihexylamino)-3-fluorophenyl)-3-oxobutanamide (3.00 g, 7.93 mmol) and ammonium bicarbonate (0.96 g, 12.0 mmol). The mixture was stirred at a certain temperature. The reaction was completed through monitoring by HPLC and then filtered. The filtrate was evaporated under reduced pressure to remove the solvent and give black oil. The reaction temperatures, reaction times and results in Embodiment 1-2 were as shown in table H.

TABLE H

| Embodiment | Reaction temperature | Reaction time | Yield |
| --- | --- | --- | --- |
| Embodiment 1 | 25° C. | 13 hours | 100% |
| Embodiment 2 | 40° C. | 3 hours | 98.6% |

Embodiment 3

To N-(4-(dihexylamino)-3-fluorophenyl)-3-oxobutanamide (51.5 g, 136 mmol) prepared from Embodiment 8 of Method Six in Example 4 which was placed in a 1000 mL single-neck flask was added anhydrous ethanol (300.0 g). The mixture was stirred into a clear solution. To the reaction mixture was added ammonium bicarbonate (22.0 g, 276 mmol), and the mixture was degassed and filled with nitrogen. Then the mixture was stirred at 40° C. in nitrogen atmosphere. The reaction was completed through monitoring by HPLC, then the reaction mixture was cooled to room temperature and filtered. The filtrate was evaporated under reduced pressure to give light brown liquid, which was used directly in the next step without further purification.

Example 6: 3-(4-(dihexylamino)-3-fluorophenyl)-2,6-dimethylpyrimidin-4(3H)-one 6-1) Preparation of the Title Compound Embodiments 1-7

(Z)-3-Amino-N-(4-(dihexylamino)-3-fluorophenyl)but-2-enamide was added into a certain amount of triethyl orthoacetate. The mixture was heated and stirred at a certain temperature. After the reaction was completed, a sample of reaction mixture was taken for HPLC detection. The reaction mixture was evaporated under reduced pressure to remove the solvent and give black liquid. The specific reaction conditions and results of Embodiments 1-7 were shown in table I.

TABLE I

| Embodiment | Triethyl orthoacetate | Temperature | Reaction time | Proportion of product |
| --- | --- | --- | --- | --- |
| Embodiment 1 | 2.0 equiv | 120° C. | 24 hours | 95.63% |
| Embodiment 2 | 3.0 equiv | 120° C. | 24 hours | 95.21% |
| Embodiment 3 | 4.0 equiv | 120° C. | 24 hours | 95.38% |
| Embodiment 4 | 3.0 equiv | 80° C. | 4 hours | 52.80% |
| Embodiment 5 | 3.0 equiv | 100° C. | 4 hours | 59.20% |
| Embodiment 6 | 3.0 equiv | 120° C. | 4 hours | 63.29% |
| Embodiment 7 | 3.0 equiv | 140° C. | 4 hours | 52.27% |

Embodiment 8

To (Z)-3-amino-N-(4-(dihexylamino)-3-fluorophenyl)but-2-enamide (51.4 g, 136 mmol) prepared from Embodiment 3 of Method Three in Example 5 which was placed in a 1000 mL single-neck flask was added triethyl orthoacetate (66.3 g, 409 mmol). The mixture was degassed and filled with nitrogen, and stirred at 120° C. under nitrogen protection, then distilled to remove the low boiling side-product. The reaction was completed through monitoring by HPLC, then the reaction mixture was evaporated under reduced pressure to remove the solvent and give black liquid, which was used directly in the next step without further purification.

6-2) Further Purification of the Title Compound
Step 1: 3-(4-(dihexylamino)-3-fluorophenyl)-2,6-dimethylpyrimidin-4(3H)-one Tosilate Embodiments 1-1 to 1-16

3-(4-(Dihexylamino)-3-fluorophenyl)-2,6-dimethylpyrimidin-4(3H)-one (0.80 g, 2.0 mmol) prepared from the method of 6-1) was dissolved in a certain solvent (5 mL). p-Toluenesulfonic acid monohydrate (0.76 g, 4.0 mmol) was added into the mixture, and the resulting mixture was stirred for 24 hours and then filtered to give a yellow solid. The solvents used in Embodiments 1-1 to 1-16 and the results were as shown in table J.

TABLE J

| Embodiment | Solvent | Yield | Purity of the product |
|---|---|---|---|
| Embodiment 1-1 | Toluene | 80.43% | 97.93% |
| Embodiment 1-2 | 1-Propanol | 75.03% | 98.81% |
| Embodiment 1-3 | n-Butanol | 71.10% | 98.25% |
| Embodiment 1-4 | t-Butanol | 83.57% | 96.85% |
| Embodiment 1-5 | Ethyl acetate | 87.14% | 97.87% |
| Embodiment 1-6 | Propanol | 86.44% | 98.99% |
| Embodiment 1-7 | Isobutanol | 80.95% | 98.39% |
| Embodiment 1-8 | Isopentanol | 74.94% | 98.20% |
| Embodiment 1-9 | n-Propyl acetate | 84.87% | 98.57% |
| Embodiment 1-10 | Isopropyl acetate | 86.62% | 95.97% |
| Embodiment 1-11 | 4-Methylpentan-2-one | 79.56% | 97.79% |
| Embodiment 1-12 | Dimethyl phthalate | 76.16% | 95.31% |
| Embodiment 1-13 | Methyl methacrylate | 84.35% | 97.27% |
| Embodiment 1-14 | 1,4-Dioxane | 82.78% | 96.92% |
| Embodiment 1-15 | Ethyl formate | 84.00% | 98.47% |
| Embodiment 1-16 | Xylene | 82.17% | 93.42% |

Embodiment 2

3-(4-(Dihexylamino)-3-fluorophenyl)-2,6-dimethylpyrimidin-4(3H)-one (660 g, 1.45 mol) prepared from the method of 6-1) was dissolved in isopropanol (4.4 L). A solution of p-toluenesulfonic acid monohydrate (558 g, 2.93 mol) in isopropanol (2.2 L) was added dropwise into the mixture. After addition, the resulting mixture was stirred at 82° C. for 10 hours and filtered by suction. The filter cake was washed with a mixed solvent of isopropanol (660 mL) and ethyl acetate (660 mL) to give a light yellow solid (808 g, 74.6%), and the purity was 98.96%.

Step 2: hydrolysis of 3-(4-(dihexylamino)-3-fluorophenyl)-2,6-dimethylpyrimidin-4(3H)-one Tosilate Embodiment 1

3-(4-(Dihexylamino)-3-fluorophenyl)-2,6-dimethylpyrimidin-4(3H)-one tosilate (5.02 kg, 6.72 mol) and potassium carbonate (3.00 kg, 21.71 mol) were added into acetonitrle (20 L). The mixture was heated to 82° C. and refluxed for 24 hours, then cooled to 30° C. and filtered. The filter cake was washed with ethyl acetate (5 L), and the filtrate was concentrated under reduced pressure to give purified 3-(4-(dihexylamino)-3-fluorophenyl)-2,6-dimethylpyrimidin-4(3H)-one as light yellow liquid, and the purity detected by HPLC was 98.82%.

Embodiment 2

3-(4-(Dihexylamino)-3-fluorophenyl)-2,6-dimethylpyrimidin-4(3H)-one tosilate (3.30 kg, 4.12 mol) and potassium carbonate (1.20 kg, 8.68 mol) were added into ethanol (16 L). The mixture was stirred at room temperature for 5.5 hours, then filtered. The filter cake was washed with dichloromethane (3 L), and the filtrate was concentrated under reduced pressure to give purified 3-(4-(dihexylamino)-3-fluorophenyl)-2,6-dimethylpyrimidin-4(3H)-one as light yellow liquid, and the purity detected by HPLC was 99.43%.

Embodiment 3

3-(4-(Dihexylamino)-3-fluorophenyl)-2,6-dimethylpyrimidin-4(3H)-one tosilate (2.17 kg, 2.90 mol) and sodium carbonate (0.71 kg, 5.14 mol) were added into ethanol (17 L). The mixture was heated to 77° C. and refluxed for 4 hours, then cooled to 30° C. and filtered. The filter cake was washed with dichloromethane (5 L), and the filtrate was concentrated under reduced pressure. The residue was dissolved in dichloromethane (10 L), and the mixture was washed with water (10 L) and saturated brine (5 L), concentrated under reduced pressure to give purified 3-(4-(dihexylamino)-3-fluorophenyl)-2,6-dimethylpyrimidin-4(3H)-one as light yellow liquid, and the purity detected by HPLC was 99.49%.

Example 7: 3-(4-(dihexylamino)-3-fluorophenyl)-2,6-dimethylpyrimidin-4(3H)-one Hydrochloride Method One:

3-(4-(Dihexylamino)-3-fluorophenyl)-2,6-dimethylpyrimidin-4(3H)-one (5.00 g, 12.3 mmol, purity: 98.63%) was dissolved in isopropanol (25 mL). The mixture was stirred at room temperature, and hydrochloric acid (1.50 g, 13.0 mmol) was added dropwise. The mixture was stirred at room temperature for 4 hours, then heated to reflux and stirred overnight. The mixture was stirred at room temperature for another 3 hours, then filtered by suction, and the filter cake was dried under vacuum in oven at 60° C. to give an off-white solid (5.02 g, 93.3%, purity: 97.12%).

Method Two:

To 3-(4-(dihexylamino)-3-fluorophenyl)-2,6-dimethylpyrimidin-4(3H)-one (54.70 g, 98.30 mmol) prepared from Embodiment 8 of 6-1) in Example 6 which was placed in a 250 mL single-neck flask was added ethyl acetate (100.0 g). The mixture was stirred into a clear solution, and then performed in nitrogen atmosphere. Concentrated hydrochloric acid (11.9 g) was added dropwise at room temperature. After addition, the mixture was heated to 80° C. and refluxed for 5 hours while water was distilled out. The reaction mixture was cooled to about 20° C. and stirred at this temperature for 12 hours, and then filtered. The filter cake was washed with ethyl acetate (35.0 g) and dried at 60° C. to give an off-white solid (43.06 g, 61.5%, purity: 99.0%).

Method Three:

Embodiments 1-3

3-(4-(Dihexylamino)-3-fluorophenyl)-2,6-dimethylpyrimidin-4(3H)-one was dissolved in a solvent. The mixture was stirred at room temperature, then to the mixture was added dropwise hydrochloric acid or hydrochloric acid solution. The mixture was stirred at a certain temperature, then filtered, and the filter cake was dried in vacuo to give an off-white solid. The specific reaction conditions and results of Embodiments 1-3 were shown in table K.

TABLE K

| Embodiment | One | Solvent/amount | Hydrochloric acid or hydrochloric acid solution | Reaction temperature and/or reaction time | Output/Yield | Purity of the product |
|---|---|---|---|---|---|---|
| Embodiment 1 | 5.00 g (Purity: 98.63%) | Ethyl acetate/50 mL | 9.8 mol/L hydrochloric acid (1.9 mL, 19 mmol) | The mixture was heated to 80° C. and stirred overnight, then cooled to room temperature and stirred for 6 hours. | 5.02 g, 93.3% | 98.63% |
| Embodiment 2 | 24.61 g (Purity: 99.24%) | DCM/100 mL | A solution of hydrochloric acid in ethyl acetate (30 mL, 30.0 mmol) | The mixture was stirred at room temperature for 2 hours. | 22.73 g, 85.3% | 99.97% |
| Embodiment 3 | 5.24 g (Purity: 99%) | Isopropanol/40 mL | A solution of hydrochloric acid in isopropanol (1.9 g, 15.6 mmol) | The mixture was stirred overnight at room temperature. | 5.29 g, 92.6% | 99.5% |

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing a compound having Formula (II) comprising reacting a compound having Formula (III) with triethyl orthoacetate at 80° C.-140° C. to give the compound having Formula (II),

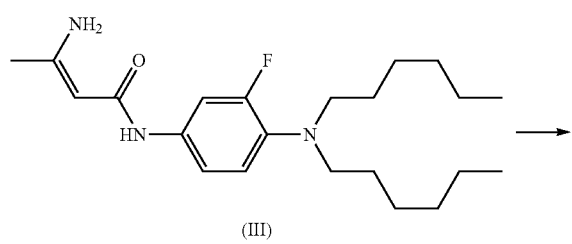

(III)

-continued

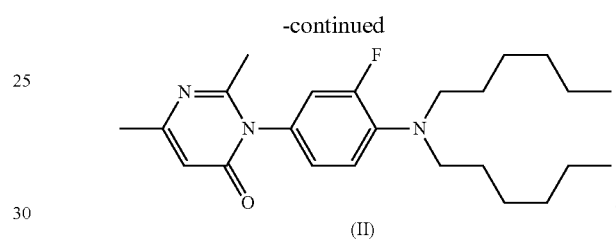

(II)

2. The method according to claim 1, wherein the reaction is carried out at 80° C.-120° C.

3. The method according to claim 1, wherein the amount of triethyl orthoacetate is 2.0 to 4.0 molar equivalents relative to the amount of compound having Formula (III).

4. The method according to claim 1, wherein the compound having Formula (II) can be further purified by the following steps:

Step (A): Reacting the compound having Formula (II) with p-toluenesulfonic acid or a p-toluenesulfonic acid hydrate in solvent 1 to give a compound having Formula (II-a);

Step (B): Reacting the compound having Formula (II-a) with base 1 in solvent 2 to give the purified compound having Formula (II);

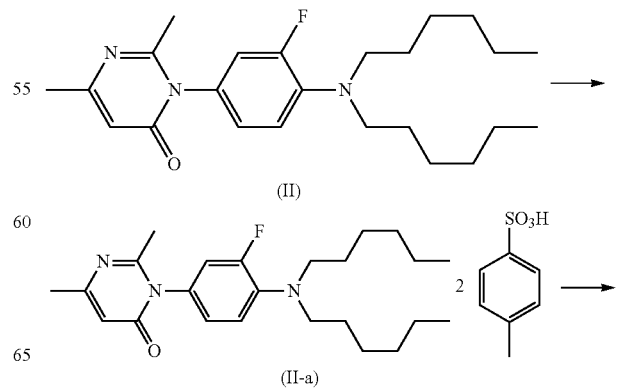

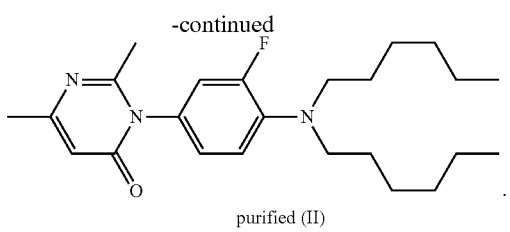

purified (II)

5. The method according to claim 4, wherein the solvent 1 is dichloromethane, acetonitrile, toluene, isopropanol, 1-propanol, n-butanol, tetrahydrofuran, t-butanol, ethyl acetate, isobutanol, isopentanol, n-propyl acetate, isopropyl acetate, 4-methyl-2-pentanone, dimethyl phthalate, methyl methacrylate, 1,4-dioxane, ethyl formate, xylene, water, or any combination thereof; and wherein the reaction in step (A) is carried out at room temperature or by heating.

6. The method according to claim 4, wherein the solvent 2 is methanol, ethanol, isopropanol, acetonitrile, or any combination thereof;

wherein the base 1 is potassium carbonate, sodium carbonate, sodium hydroxide, potassium hydroxide, lithium hydroxide, sodium bicarbonate, potassium bicarbonate, or any combination thereof; and the reaction in step (B) is carried out at room temperature or by heating.

7. The method according to claim 1 further comprising a method for preparing the compound having Formula (III) which comprises reacting a compound having Formula (IV) with a solution of ammonia in alcohol or an ammonium salt in solvent 5 to give the compound having Formula (III);

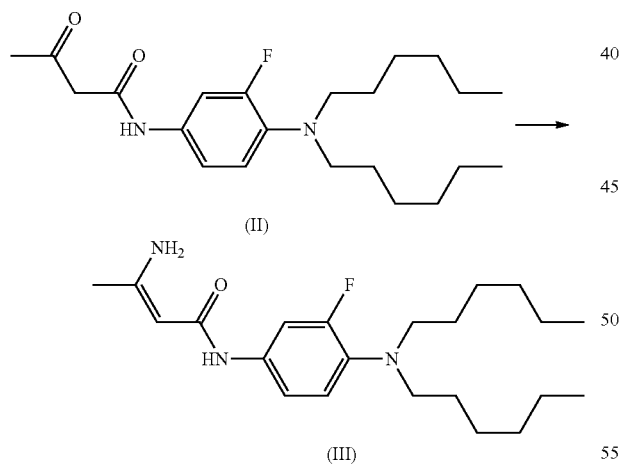

wherein the solvent 5 is methanol, ethanol, isopropanol, water, or any combination thereof;

the reaction is carried out at 20° C.-65° C.; or the reaction is carried out at room temperature;

the solution of ammonia in alcohol is a solution of ammonia in methanol; and the ammonium salt is ammonium chloride, ammonium bromide, ammonium acetate, ammonium formate, or ammonium bicarbonate.

8. The method according to claim 7, wherein the reaction of compound having Formula (IV) with an ammonium salt is carried out in the presence of base a;

wherein the base a is triethylamine, N,N-diisopropylethylamine, pyridine, potassium carbonate, sodium carbonate, sodium hydroxide, potassium hydroxide, lithium hydroxide, sodium bicarbonate, potassium bicarbonate, or any combination thereof.

9. The method according to claim 7, wherein the amount of ammonia in the solution of ammonia in methanol is 2.0 to 4.0 molar equivalents relative to the amount of the compound having Formula (IV).

10. The method according to claim 7 further comprising a method for preparing the compound having Formula (IV) which comprises reacting a compound having Formula (V) with diketene or an acetoacetate in solvent 6 to give the compound having Formula (IV),

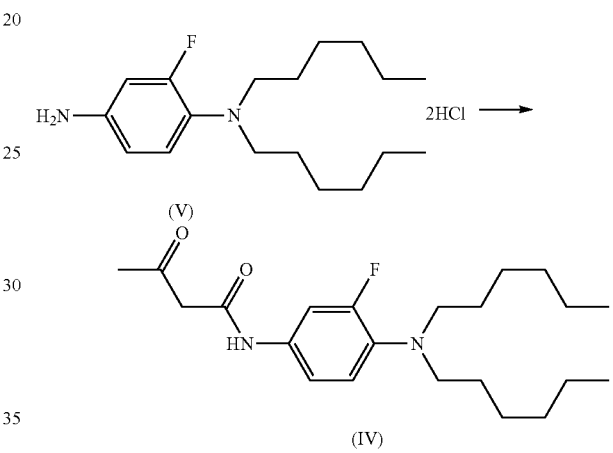

wherein the solvent 6 is dichloromethane, tetrahydrofuran, toluene, acetone, acetonitrile, water, or any combination thereof;

wherein the reaction is carried out at 0° C.-110° C.; and the acetoacetate is methyl acetoacetate, ethyl acetoacetate, isopropyl acetoacetate or tert-butyl acetoacetate.

11. The method according to claim 10, wherein the reaction is carried out in the presence of base 2;

wherein the base 2 is triethylamine, N,N-diisopropylethylamine, pyridine, methylmorpholine, potassium carbonate, sodium carbonate, sodium hydroxide, potassium hydroxide, lithium hydroxide, sodium bicarbonate, potassium bicarbonate, or any combination thereof.

12. The method according to claim 10, wherein the reaction of compound having Formula (V) with diketene is carried out at 0° C.-42° C., or about 0° C., or room temperature, or about 42° C.;

the reaction of the compound having Formula (V) with an acetoacetate is carried out by heating at 105° C.-110° C., or about 105° C., or about 110° C.

13. The method according to claim 10, wherein the amount of diketene is 1.0 to 2.0 molar equivalents relative to the amount of the compound having Formula (V); or, the amount of diketene is about 1.0, 1.2, 1.5 or 2.0 molar equivalents relative to the amount of the compound having Formula (V).

14. The method according to claim 10 further comprising a method for preparing the compound having Formula (V) which comprises reacting a compound having Formula (VI) with a suitable reagent in solvent 7 to give the compound having Formula (V),

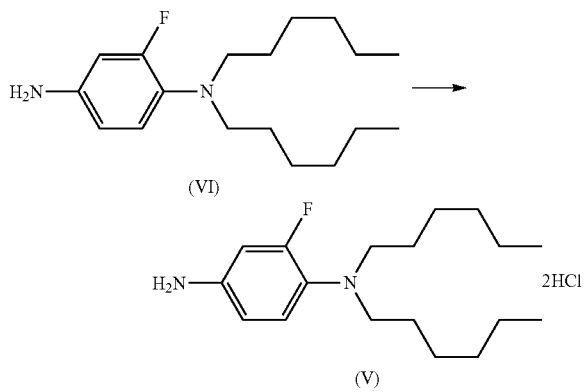

wherein the solvent 7 is ethyl acetate, acetone, toluene, acetonitrile, methanol, ethanol, dichloromethane or a combination thereof;
the suitable reagent is hydrogen chloride or a hydrogen chloride solution, Me₃SiCl or SOCl₂; and
the reaction is carried out at room temperature.

15. The method according to claim 14 further comprising a method for preparing the compound having Formula (VI)

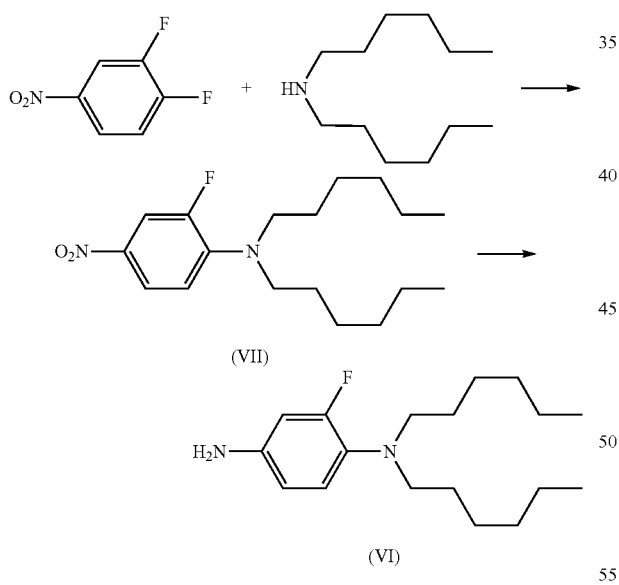

which comprises
Step (i): Reacting 3,4-difluoronitrobenzene with dihexylamine in the presence of base 3 in solvent 8 to give a compound having Formula (VII);
wherein, the reaction is carried out at 80° C.-90° C.;
the solvent 8 is N,N-dimethylformamide, toluene, ethyl acetate, acetonitrile, acetone, isopropanol, ethanol, or any combination thereof;
the base 3 is lithium hydroxide or a hydrate thereof, sodium carbonate, potassium carbonate, sodium bicarbonate, potassium bicarbonate, potassium phosphate, sodium phosphate, sodium hydroxide, potassium hydroxide, triethylamine, pyridine, or any combination thereof; and
Step (ii): Reacting the compound having Formula (VII) in the presence of a reductant in solvent 9 to give the compound having Formula (VI);
wherein, the reaction is carried out at room temperature or at 65° C.-100° C.;
the solvent 9 is methanol, ethanol, isopropanol, tetrahydrofuran, ethyl acetate, water or any combination thereof;
the reductant is Zn, Fe, SnCl₂ or a hydrate thereof, Na₂S or a hydrate thereof, a mixture of Na₂S or a hydrate thereof and S, Na₂S₂ or a hydrate thereof, PtO₂ or Raney nickel.

16. The method according to claim 15, wherein, the reaction in step (i) is further carried out in the presence of cuprous iodide; and
the reaction in step (ii) is further carried out in the presence of an acidic reagent, wherein the acidic reagent is HCl, AcOH or NH₄Cl.

17. A method for preparing a compound having Formula (II) comprising:

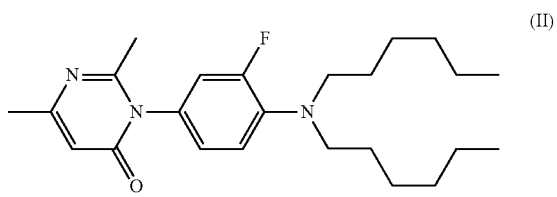 [SMILES: CCCCCCN(CCCCCC)c1ccc(-n2c(C)nc(C)cc2=O)cc1F]

Step I): reacting 3,4-difluoronitrobenzene with dihexylamine in the presence of base 3 in solvent 8 at about 80° C. to give a compound having Formula (VII);

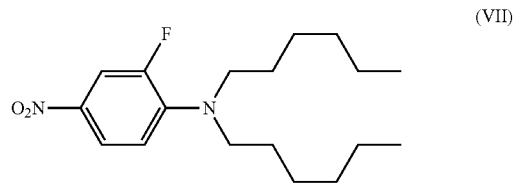

wherein, the solvent 8 is N,N-dimethylformamide, toluene, acetonitrile, isopropanol, ethanol, or any combination thereof; the base 3 is lithium hydroxide or a hydrate thereof, sodium carbonate, potassium carbonate, sodium bicarbonate, potassium bicarbonate, potassium phosphate, sodium phosphate, sodium hydroxide, potassium hydroxide, or any combination thereof;
Step II): reacting the compound having Formula (VII) in the present of a reductant in solvent 9 at about 80° C. to give compound having Formula (VI);

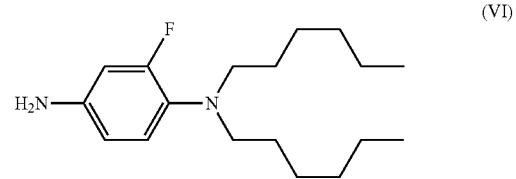

wherein, the solvent 9 is methanol, ethanol, isopropanol, water or any combination thereof; the reductant is Na₂S or a hydrate thereof, or a mixture of Na₂S or a hydrate thereof and S;

Step III): reacting a compound having Formula (VI) with a suitable reagent in solvent 7 at room temperature to give the compound having Formula (V),

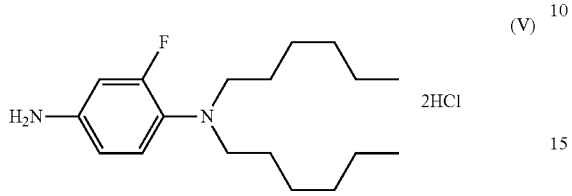

wherein, the solvent 7 is ethyl acetate, methanol, ethanol, or a combination thereof; the suitable reagent is hydrogen chloride, a hydrogen chloride solution, or Me₃SiCl;

Step IV): reacting a compound having Formula (V) with an acetoacetate in solvent 6 at about 105° C. to about 110° C. to give the compound having Formula (IV),

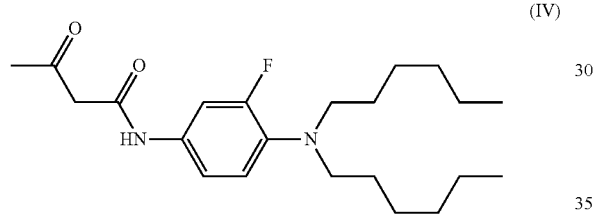

wherein the solvent 6 is toluene, water, or any combination thereof; the acetoacetate is methyl acetoacetate, ethyl acetoacetate, isopropyl acetoacetate or tert-butyl acetoacetate;

Step V): reacting a compound having Formula (IV) with an ammonium salt in solvent 5 at about 25° C. to about 40° C. to give the compound having Formula (III);

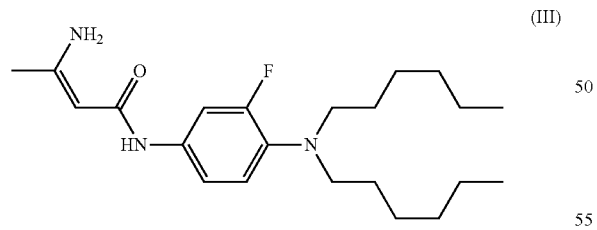

wherein the solvent 5 is methanol, ethanol, isopropanol, water, or any combination thereof; the ammonium salt is ammonium chloride, ammonium bromide, ammonium acetate, ammonium formate, or ammonium bicarbonate;

Step VI): reacting a compound having Formula (III) with triethyl orthoacetate at 80° C.-140° C., wherein the amount of triethyl orthoacetate is 2.0 to 4.0 molar equivalents relative to the amount of the compound having Formula (III).

18. The method according to claim 17, wherein the reaction of Step IV) may be carried out in the present of base 2 which is triethylamine, N,N-diisopropylethylamine, pyridine, methylmorpholine, potassium carbonate, sodium carbonate, sodium bicarbonate, potassium bicarbonate, or any combination thereof; and the reaction of Step V) may be carried out in the present of base a which is potassium carbonate, sodium carbonate, sodium bicarbonate, potassium bicarbonate, or any combination thereof.

19. A method for preparing a compound having Formula (II) comprising:

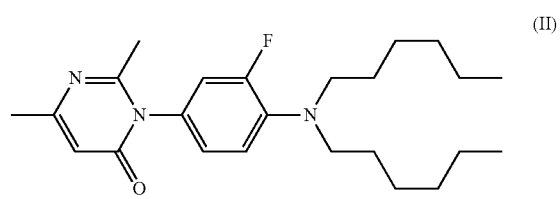 [SMILES: CCCCCCN(CCCCCC)c1ccc(-n2c(C)nc(C)cc2=O)cc1F]

Step Ia): reacting 3,4-difluoronitrobenzene with dihexylamine in the presence of base 3 in solvent 8 at about 80° C. to give a compound having Formula (VII);

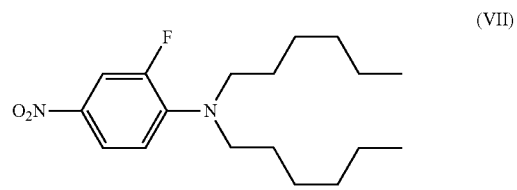

wherein, the solvent 8 is N,N-dimethylformamide, toluene, acetonitrile, isopropanol, ethanol, or any combination thereof; the base 3 is lithium hydroxide or a hydrate thereof, sodium carbonate, potassium carbonate, sodium bicarbonate, potassium bicarbonate, potassium phosphate, sodium phosphate, sodium hydroxide, potassium hydroxide, or any combination thereof;

Step IIa): reacting the compound having Formula (VII) in the present of a reductant in solvent 9 at about 80° C. to give compound having Formula (VI);

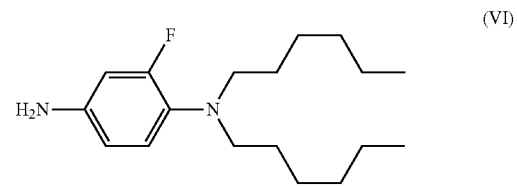

wherein, the solvent 9 is methanol, ethanol, isopropanol, water or any combination thereof; the reductant is Zn, Fe, Na₂S or a hydrate thereof, a mixture of Na₂S or a hydrate thereof and S;

Step IIIa): reacting a compound having Formula (VI) with a suitable reagent in solvent 7 at room temperature to give the compound having Formula (V),

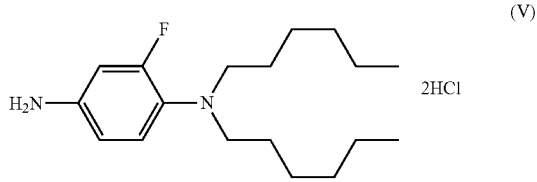

wherein, the solvent 7 is ethyl acetate, methanol, ethanol, or a combination thereof; the suitable reagent is hydrogen chloride, a hydrogen chloride solution, or Me₃SiCl;

Step IVa): reacting a compound having Formula (V) with diketene in the present of base 2 in solvent 6 at room temperature to give the compound having Formula (IV),

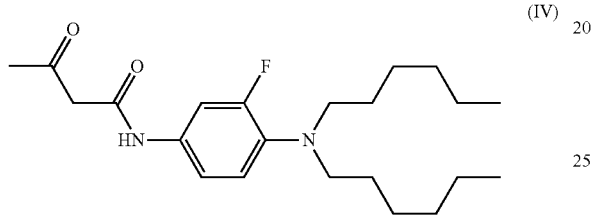

wherein the solvent 6 is dichloromethane, tetrahydrofuran, toluene, acetone, acetonitrile, water, or any combination thereof; the base 2 is triethylamine, N,N-diisopropylethylamine, potassium carbonate, sodium carbonate, sodium bicarbonate, or potassium bicarbonate;

Step Va): reacting a compound having Formula (IV) with a solution of ammonia in alcohol in solvent 5 at about 40° C. to about 65° C. to give the compound having Formula (III);

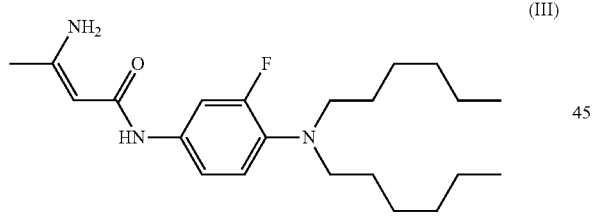

wherein the solvent 5 is methanol, ethanol, isopropanol, water, or any combination thereof; the solution of ammonia in alcohol is a solution of ammonia in methanol;

the amount of ammonia in the solution of ammonia in methanol is 2.0 to 4.0 molar equivalents relative to the amount of the compound having Formula (IV);

Step VIa): reacting a compound having Formula (III) with triethyl orthoacetate at 80° C.-140° C.;

wherein the amount of triethyl orthoacetate is 2.0 to 4.0 molar equivalents relative to the amount of the compound having Formula (III).

20. The method according to claim 19, wherein the reaction of Step Ia) is further carried out in the presence of cuprous iodide; and the reaction of Step IIa) is further carried out in the presence of an acidic reagent, wherein the acidic reagent is HCl, AcOH or NH₄Cl.

21. A compound having Formula (V),

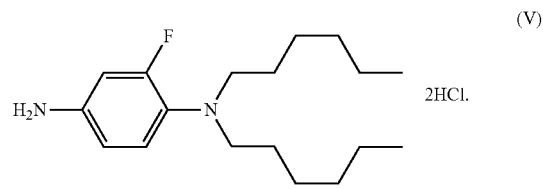 [SMILES: CCCCCCN(CCCCCC)c1ccc(N)cc1F]

22. A method for preparing a compound having Formula (I) comprising reacting a compound having Formula (II) prepared by the method of claim 1 with hydrogen chloride or a hydrogen chloride solution in solvent 3 to give the compound having Formula (I),

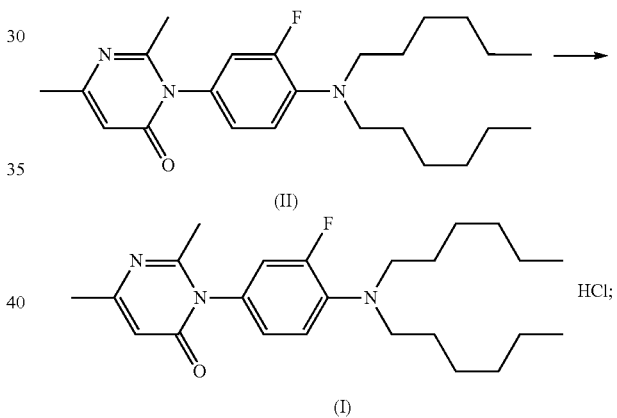

wherein the solvent 3 is dichloromethane, ethyl acetate, ethanol, isopropanol, tert-butanol, water, or any combination thereof;

the hydrogen chloride solution is a solution of hydrogen chloride in water, a solution of hydrogen chloride in ethyl acetate or a solution of hydrogen chloride in isopropanol; and the reaction is carried out at room temperature or by heating; wherein heating refers to heating to reflux, or heating to about 80° C.

* * * * *